(12) United States Patent
Kanner

(10) Patent No.: US 8,263,016 B2
(45) Date of Patent: Sep. 11, 2012

(54) ADDITIVE EFFECT ENHANCED HYDROGEN PEROXIDE DISINFECTION METHOD AND APPARATUS

(75) Inventor: Rowland W. Kanner, Guntersville, AL (US)

(73) Assignee: Atrion Medical Products, Inc., Arab, AL (US)

( * ) Notice: Subject to any disclaimer, the term of this patent is extended or adjusted under 35 U.S.C. 154(b) by 329 days.

(21) Appl. No.: 12/604,148

(22) Filed: Oct. 22, 2009

(65) Prior Publication Data

US 2010/0233041 A1 Sep. 16, 2010

Related U.S. Application Data

(60) Provisional application No. 61/160,488, filed on Mar. 16, 2009, provisional application No. 61/162,881, filed on Mar. 24, 2009, provisional application No. 61/166,932, filed on Apr. 6, 2009, provisional application No. 61/171,175, filed on Apr. 21, 2009.

(51) Int. Cl.
*A61L 2/00* (2006.01)
*A61L 9/00* (2006.01)

(52) U.S. Cl. ........ 422/301; 422/292; 422/295; 422/296; 422/297; 422/300

(58) Field of Classification Search .......... 422/292, 422/295, 296, 297, 300, 301, 28, 29, 30
See application file for complete search history.

(56) References Cited

U.S. PATENT DOCUMENTS

| | | | |
|---|---|---|---|
| 2,170,485 A | 8/1939 | Reilly | |
| 3,770,113 A | 11/1973 | Thomas | |
| 4,013,410 A | 3/1977 | Thomas et al. | |
| 4,151,253 A * | 4/1979 | Waggoner et al. | 422/295 |
| 4,200,187 A | 4/1980 | Thomas | |
| 4,637,919 A | 1/1987 | Ryder et al. | |
| 4,750,610 A * | 6/1988 | Ryder | 206/5.1 |
| 4,807,750 A | 2/1989 | Ryder et al. | |
| 4,817,998 A | 4/1989 | Ryder et al. | |
| 4,889,693 A | 12/1989 | Su et al. | |
| 4,890,729 A | 1/1990 | Ranalletta | |
| 4,956,156 A | 9/1990 | Kanner et al. | |
| 4,981,657 A | 1/1991 | Ryder | |
| 5,059,402 A | 10/1991 | Seamons et al. | |
| 5,143,104 A | 9/1992 | Iba et al. | |
| 5,196,174 A | 3/1993 | Cerola et al. | |
| 5,250,266 A | 10/1993 | Kanner | |
| 5,292,488 A | 3/1994 | Cerola et al. | |
| 5,306,352 A | 4/1994 | Nicolson et al. | |
| 5,366,078 A | 11/1994 | Braun | |
| 5,388,686 A * | 2/1995 | Kanner et al. | 206/5.1 |
| 5,468,448 A | 11/1995 | Nicolson et al. | |
| 5,558,846 A | 9/1996 | Alvord et al. | |
| 5,609,837 A | 3/1997 | Cerny et al. | |
| 5,690,211 A | 11/1997 | Jao et al. | |
| 5,756,044 A * | 5/1998 | Mowrey-McKee et al. | 422/28 |
| 5,958,351 A | 9/1999 | Cerny et al. | |
| 6,503,507 B1 | 1/2003 | Allen | |

(Continued)

*Primary Examiner* — Regina M. Yoo
(74) *Attorney, Agent, or Firm* — Clark Hill PLC

(57) ABSTRACT

A method which enhances a disinfection process by obtaining an additive effect from energy and byproducts of the decomposition process. Also disclosed are contact lens disinfecting systems, wherein the systems are configured to create the desirable elevated pressure, oxygen saturation and sustained peroxide concentration conditions within a contact lens holding and reaction chamber, in order to enhance disinfection by additive effect. The systems are configured to provide that an elevated pressure is maintained in the reaction chamber before venting occurs.

20 Claims, 27 Drawing Sheets

U.S. PATENT DOCUMENTS

| | | |
|---|---|---|
| 6,702,033 B1 * | 3/2004 | Mitchell et al. ............... 169/85 |
| 7,198,760 B1 * | 4/2007 | Wagner ...................... 422/108 |
| 8,038,939 B2 | 10/2011 | Kanner |
| 8,039,245 B2 | 10/2011 | Kanner |
| 2001/0017271 A1 | 8/2001 | Yavitz |
| 2005/0087453 A1 | 4/2005 | Mahieu et al. |
| 2005/0263412 A1 | 12/2005 | Huang |
| 2006/0127289 A1 * | 6/2006 | Selig et al. ................... 422/300 |
| 2007/0042066 A1 | 2/2007 | Nitsche et al. |
| 2008/0047590 A1 | 2/2008 | Weill et al. |
| 2008/0185298 A1 | 8/2008 | Kanner et al. |

* cited by examiner

ADDITIVE EFFECT ENHANCED HYDROGEN PEROXIDE DISINFECTION METHOD AND APPARATUS

RELATED APPLICATIONS

Priority Claim

This application claims the benefit of the following United States Provisional Applications, all of which are incorporated herein by reference in their entirety: U.S. Provisional Application Ser. No. 61/160,488, filed Mar. 16, 2009; U.S. Provisional Application Ser. No. 61/162,881, filed Mar. 24, 2009; U.S. Provisional Application Ser. No. 61/166,932, filed Apr. 6, 2009; and U.S. Provisional Application Ser. No. 61/171,175, filed Apr. 21, 2009.

BACKGROUND

The present invention generally relates to methods and apparatus for controlling the decomposition of a solution using a catalyzing agent, and more specifically relates to a method and apparatus for controlling and enhancing a disinfection process by additive effect.

The present invention relates to an improved disinfection method and apparatus which utilizes, for example, hydrogen peroxide solution and a catalyzing agent to facilitate controlled decomposition of the hydrogen peroxide within a sealed reaction chamber containing an object to be disinfected, such as contact lenses, wherein the solution, the decomposition catalyzing agent, the resulting energy, and byproducts of decomposition are employed to control and enhance the disinfection process by additive effect.

While the method disclosed herein may be utilized, for example, to disinfect contact lenses, particularly soft contact lenses, the method may also be suitable to disinfect other types of items, for example larger items, such as non-sterile medical or dental appliances and the like, within a reaction chamber appropriately scaled to size. As such, while the present disclosure focuses on using the method (and associated apparatus) to disinfect contact lenses using hydrogen peroxide, it should be understood that the method can be used in other disinfecting applications.

Hydrogen peroxide is unstable and eventually decomposes (disproportionates) into water and oxygen over time. The decomposition occurs more quickly if the hydrogen peroxide is, for example, subjected to temperature extremes, exposed to ultraviolet light, or introduced to a catalyzing agent. The decomposition rate is also affected by its percentage of concentration, its pH, and the presence of impurities and stabilizers. The decomposition process is exothermic in nature and when a catalyzing agent has been introduced to the hydrogen peroxide, evolved thermal energy and oxygen can accelerate the process by several means that increase molecular contact opportunities with the catalyzing agent. The means include creation of thermally inspired convection, mechanical mixing resulting from the stirring effect of rising oxygen bubbles, as well as increased molecular motion which lowers the energy threshold for decomposition.

Hydrogen peroxide is a larger molecule than water with a specific gravity of 1.443 and a viscosity of 1.245 cP at 20 degrees Celsius, compared to water which has a viscosity of 1.003 cP at 20 degrees Celsius. Nevertheless, each is entirely miscible with the other, allowing a limitless variety of concentration levels to be tailored to suit various applications. Hydrogen peroxide solutions formulated for disinfection may contain surfactants, and are often pH-modified and chemically-stabilized in order to assure reasonable shelf life and potency at the time of use. Hydrogen peroxide formulated for disinfection of contact lenses, for example, is generally supplied at a concentration of no less than 3.0%, and may range up to 4.0% in order to assure that a minimum concentration of 3.0% is available for disinfection.

While more highly concentrated solutions would be more potent and effective against pathogens, the use of more highly concentrated solutions has generally not been pursued for contact lens care use. This is due to the strong oxidizing nature of hydrogen peroxide, and the damaging effects such higher concentrations could have upon accidental, full strength contact with sensitive ocular tissue.

Catalysts that facilitate decomposition of hydrogen peroxide include most of the transition metals, manganese dioxide, silver and the enzyme catalase. Quite commonly in connection with single step contact lens disinfection systems, platinum is introduced to the solution in the form of a surface coating on a polymeric support structure. Catalysts function by changing the energy pathway for a chemical reaction. FIG. 1 provides a graph which compares the energy associated with activating without a catalyst (line 10) to the energy associated with activating with a catalyst (line 12). As indicated, when introduced to hydrogen peroxide, a catalyst serves to lower the activation energy required to initiate decomposition of the hydrogen peroxide under ambient conditions in which it was otherwise stable.

The combination of solution temperature, exothermally-generated heat, thermally-inspired convection, mechanical stirring from evolving oxygen bubbles, dilution resulting from disproportionation, dissolved gas in the solution, and changes in ambient pressure has been found to impact the rate at which the catalyzed reaction progresses. In an open environment such as that provided by a typical commercially-available hydrogen peroxide disinfection cup system for contact lenses, for example the AO SEPT system (as shown in FIG. 2, with the overall system being identified with reference numeral 13) offered by Ciba Vision, contact lenses are introduced to 10 milliliters of the hydrogen peroxide solution essentially simultaneously with the catalyst, and evolved oxygen from the reaction is subsequently vented off through a hydrophobic membrane or one way valve (indicated with reference numeral 14 in FIG. 2) in the cap (indicated with reference numeral 15 in FIG. 2). As shown in FIG. 3, with this type of system, solution concentration resulting from the catalyzed reaction declines rather rapidly to about 0.1%, whereupon six to eight hours are required before the concentration of the solution bath has been reduced to a level that is safe for a disinfected lens to be inserted in the eye without risk of ocular irritation to the user.

Disinfection of contact lenses is regularly practiced by lens wearers in order to eliminate a variety of environmentally ubiquitous organisms known to be found on contaminated lenses. The organisms at issue include, but are not limited to, various pathogenic strains of *Staphylococcus, Pseudomonas, E. Coli, Acanthamoeba*, and the like. *Acanthamoeba* is an opportunistic pathogen associated with a potentially blinding infection of the cornea termed *Acanthamoeba keratitis*. Among the general population, contact lens wearers are believed to be most at risk to this organism, accounting for more than 95% of reported cases of the ocular infection. A particularly insidious organism, *Acanthamoeba* can transition from active trophozoite to a dormant, more resistant encysted stage when exposed to conditions of starvation, desiccation, and changes in pH and temperature. Once encysted, this organism's resistance to biocides results largely from the physical barrier of its cyst walls rather than as a consequence of metabolic dormancy. The major components of the cyst's walls are acid-resistant proteins and cellulose, with the outer wall, or exocyst, composed primarily of protein and the inner endocyst comprised of over 30% cellulose. Although remarkably resistant to chlorine-bearing disinfectants and even hydrochloric acid, encysted *Acanthamoeba* is subject to destruction by exposure to hydrogen peroxide.

Under standard ambient conditions, the method by which hydrogen peroxide destroys pathogens is through oxidation resulting in denaturation of the organism's proteins. One option to deal with heavily contaminated lenses or resistant organisms, such as *Acanthamoeba*, would be to start with a more highly concentrated solution, but there are undesirable user risks associated with that approach. Some of these risks have already been discussed hereinabove.

A more attractive option would be to slow the decomposition process in order to maintain a higher concentration of hydrogen peroxide for a longer period of time before finally reducing the concentration to an ocularly comfortable level. With such an approach, more heavily contaminated lenses could therefore be disinfected, and resistant organisms could be better dealt with using solutions that have commonly-accepted concentrations. Unfortunately, present day disinfection systems are limited by the reaction rate necessary to obtain irritation-free disinfected lenses at the end of a reasonable 6 to 8 hour overnight wait period. This results from a balance that has historically been struck between the volume of peroxide solution, a safe and practical starting concentration level for the peroxide, and the size of catalyst (such as platinum) necessary to assure adequate decomposition in use. Regarding catalyst size, typically 94 square millimeters to 141 square millimeters of catalyst surface area is allocated for each milliliter of 3.0% to 4.0% hydrogen peroxide solution. Although an undersized catalyst would certainly slow the decomposition process, using an undersized catalyst may result in the lens solution not reaching user comfort levels within a reasonable time period, since the significance of catalyst surface area actually increases as the amount of released energy and solution concentration declines. Additionally, methods (such as is disclosed in U.S. Pat. No. 5,468,448) of slowing decomposition by using buoyant catalysts that have contact areas which increase as they sink from loss of attached bubbles have proven too difficult to commercialize reliably.

OBJECTS AND SUMMARY

An object of an embodiment of the present invention is to provide an improved disinfection method.

Another object of an embodiment of the present invention is to provide an apparatus which can be used to practice the method.

Briefly, a specific embodiment of the present invention provides a method which can be used to disinfect, for example, contact lenses using hydrogen peroxide and a catalyst. The method provides that once the catalyst is introduced to the hydrogen peroxide in a reaction chamber, such as in a contact lens case, and the reaction chamber is sealed, the hydrostatic pressure within the reaction chamber is allowed to reach a relatively high level before venting takes place. Allowing the hydrostatic pressure within the reaction chamber to achieve a relatively high level before venting provides for a hydrogen peroxide disinfection process which is enhanced by additive affect.

BRIEF DESCRIPTION OF THE DRAWINGS

The organization and manner of the structure and operation of the invention, together with further objects and advantages thereof, may best be understood by reference to the following description, taken in connection with the accompanying drawing, wherein.

DESCRIPTION

Figure 1:
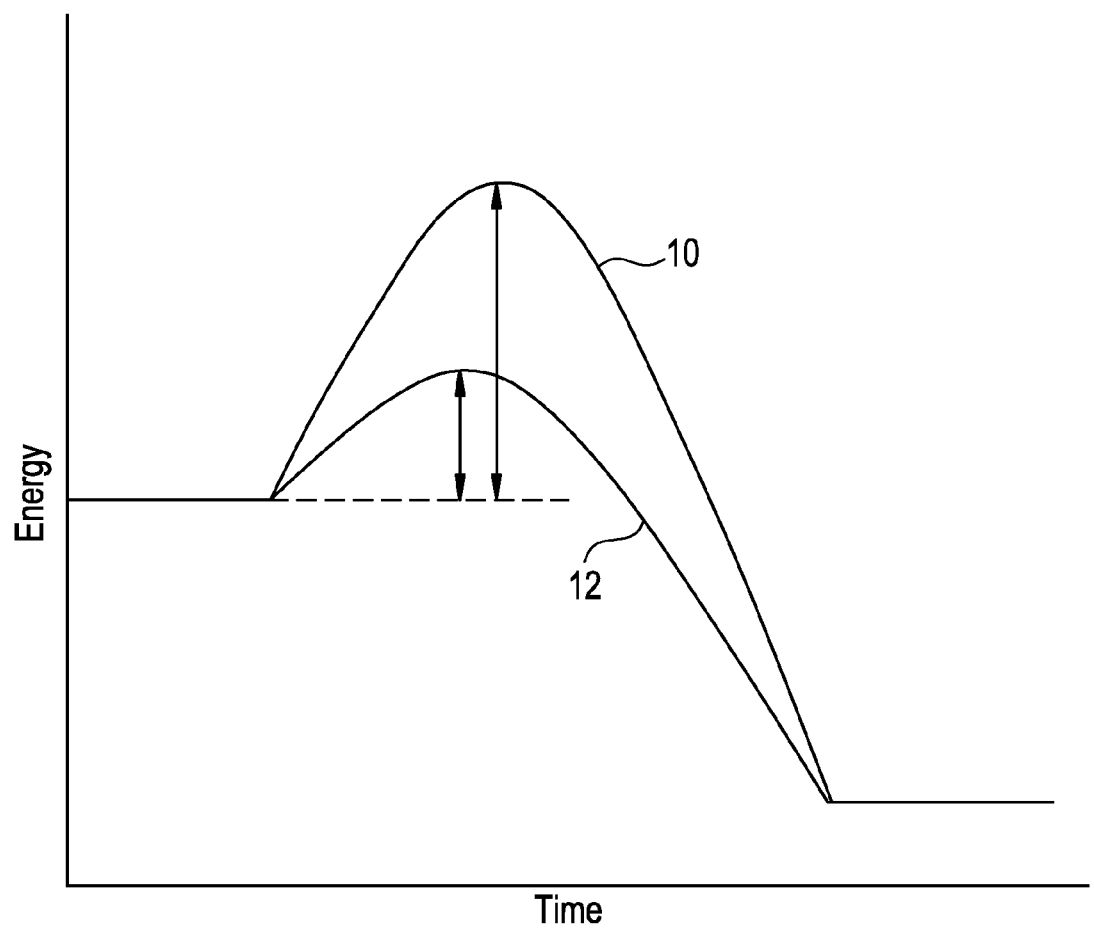
FIG. 1 is a graph which effectively compares the energy associated with activating without a catalyst to the energy associated with activating with a catalyst.

The inventions disclosed herein are susceptible to embodiment in many different forms. However, specific embodiments are shown in the drawings and described in detail hereinbelow. The present disclosure is to be considered an example of the principles of the invention, and is not intended to limit the invention to the specific embodiments which are illustrated and described herein.

The method disclosed herein enhances the disinfection process by obtaining an additive effect from energy and byproducts of the decomposition process. Useful energy is available during the catalytically-inspired disproportionation of hydrogen peroxide solution in the form of heat and expansion of evolved oxygen molecules.

Figure 2:
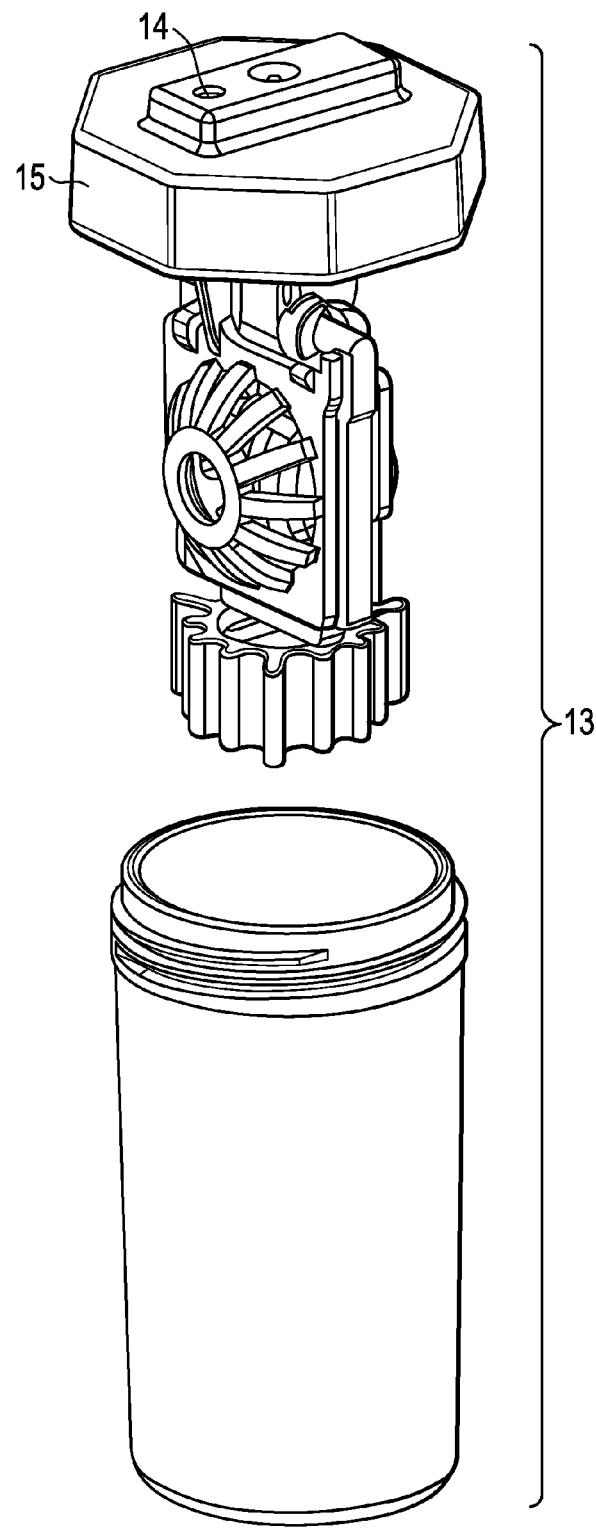
FIG. 2 is a perspective view of a prior art contact lens disinfection cup system, specifically the AO SEPT system offered by Ciba Vision.
Figure 3:
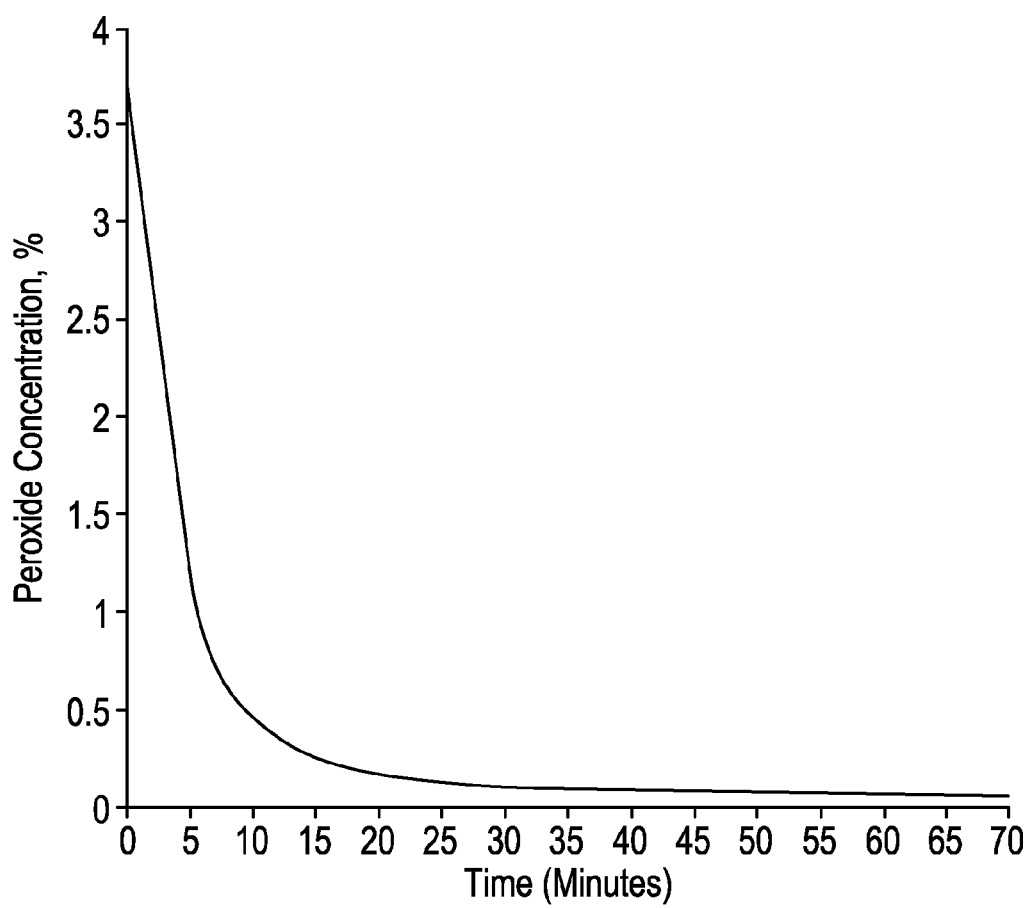
FIG. 3 is a graph which indicates the change in concentration of a hydrogen peroxide solution over time, when the cup system shown in FIG. 2 is used to disinfect contact lenses.
Figure 4:
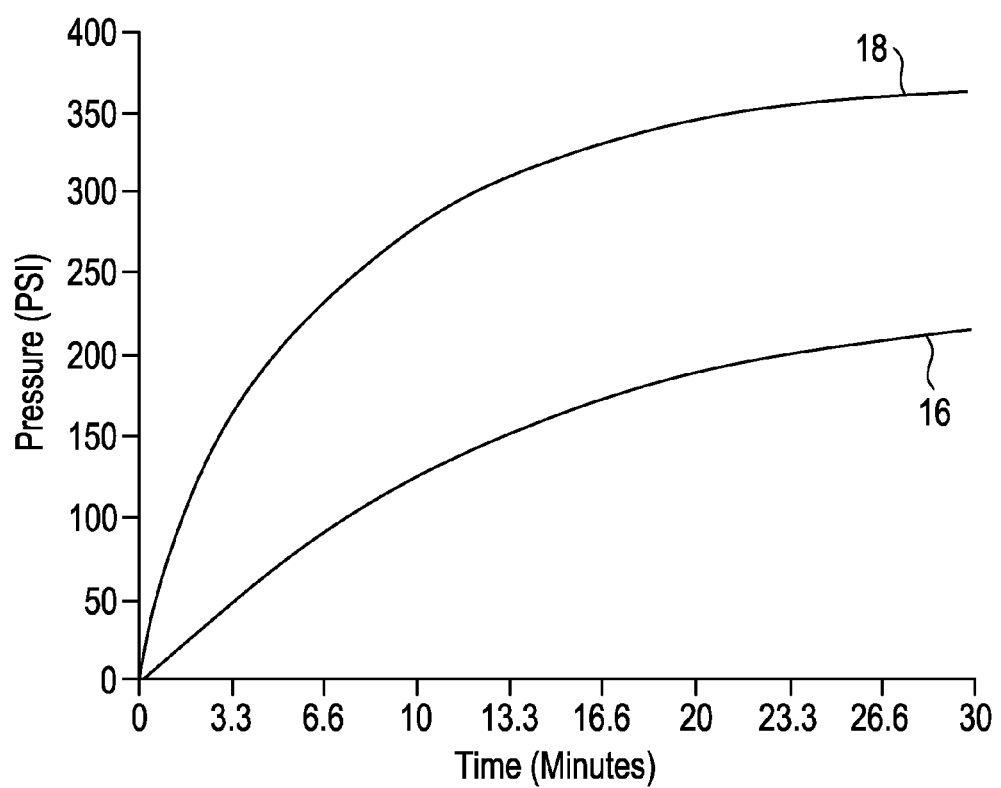
FIG. 4 is a graph which indicates the change in pressure over time, comparing the use of a catalyst having a given surface area, to the use of a catalyst having twice the surface area.
Figure 6:
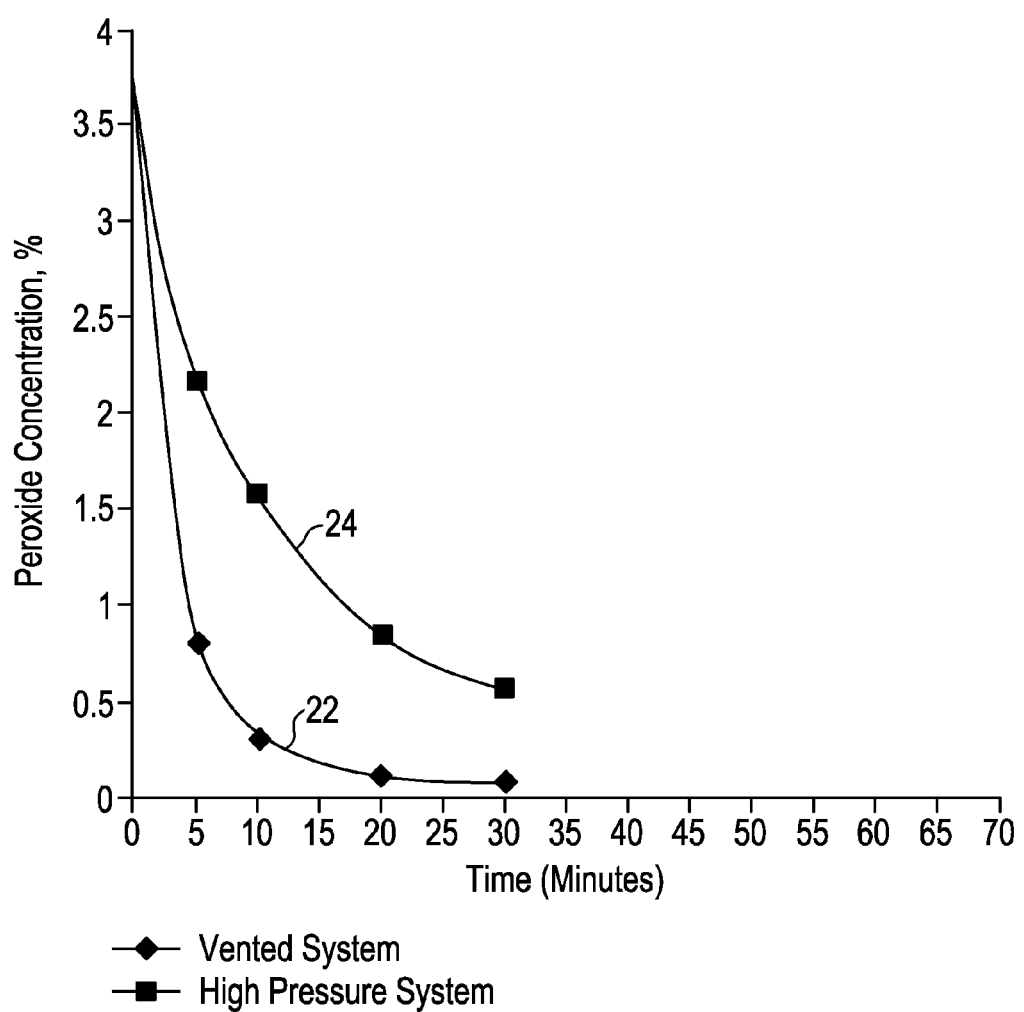
FIG. 6 is a graph which indicates the change in peroxide concentration over time, comparing a vented system to a high pressure system.
Figure 7:
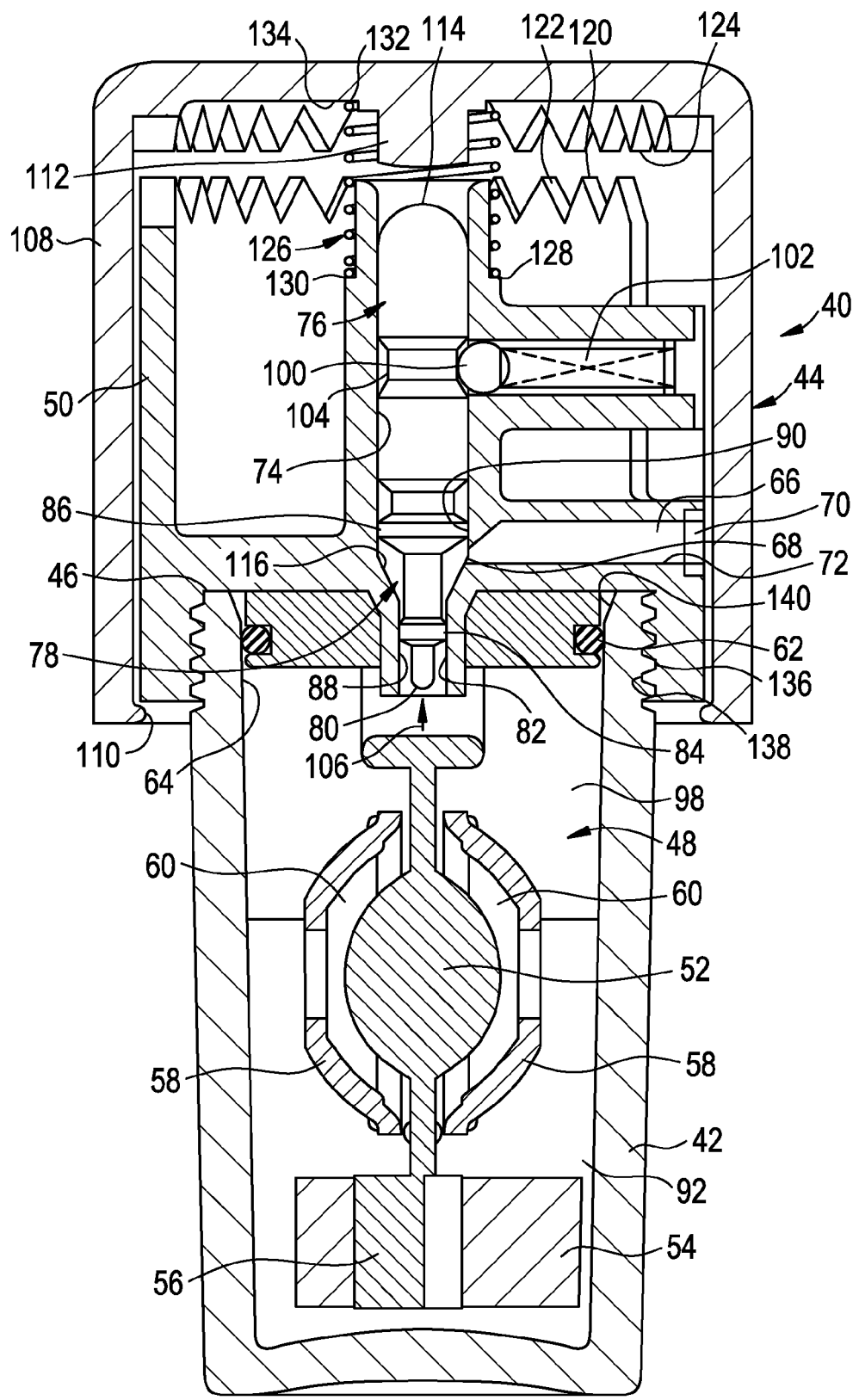
FIGS. 7 and 8 are cross-sectional views of a contact lens disinfecting system, wherein the system is configured to create desirable elevated pressure, oxygen saturation, sustained peroxide concentration conditions, and rapid decompression, in order to enhance disinfection by additive effect.
Figure 8:
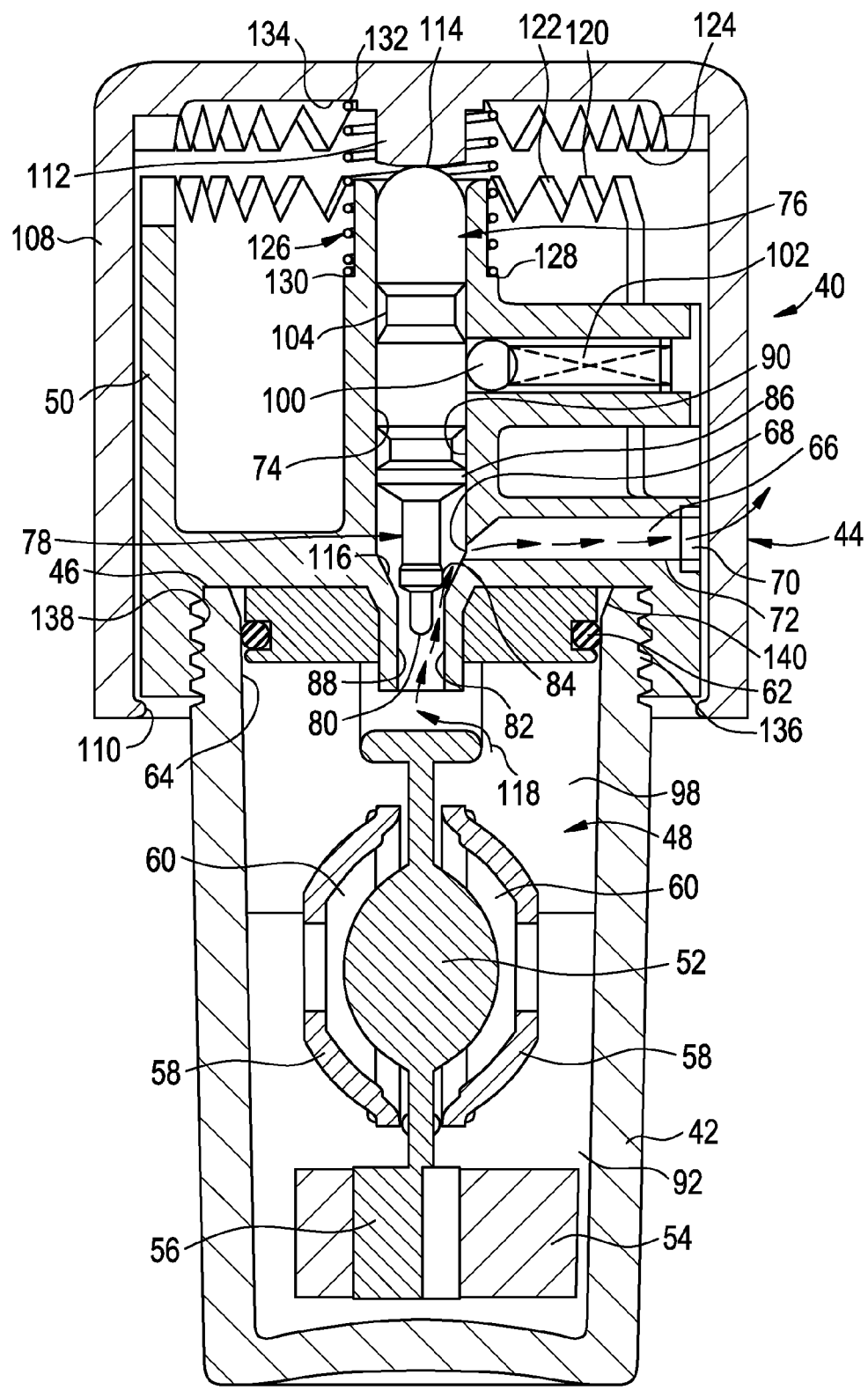

As will be described more fully later hereinbelow, FIGS. 7 and 8 illustrate a contact lens disinfection system which is in accordance with an embodiment of the present invention, and is configured to allow internal pressure to become somewhat significant before venting takes place. FIG. 4 is a graph which indicates the change in internal pressure over time, when a system such as is shown in FIGS. 7 and 8 is employed, comparing the use of a catalyst having a given surface area (represented in FIG. 4 by the curve identified with reference numeral 16), to the use of a catalyst having twice the surface area (represented in FIG. 4 by the curve identified with reference numeral 18). As shown, containment of the liberated oxygen from 10 milliliters of solution within a reaction chamber having 4 cc of head space, a volume similar to the typical contact lens cup discussed above (and illustrated in FIG. 2), has the potential to generate approximately 186 p.s.i. pressure within one half hour following introduction of a catalyst having 948 square millimeters of surface area, and as much as 366 p.s.i. in one half hour upon introduction of a catalyst having twice that surface area. As can be seen in FIG. 6, either catalyst has the ability to raise internal pressures to 100 p.s.i. within 9 minutes at which time the peroxide concentration shown in FIG. 6, line 24 is over 4 times greater than that of the vented system (line 22).

Although a catalyst having more than 94 to 141 square millimeters of surface area for each cubic centimeter of solution would serve to decrease hydrogen peroxide solution concentration too quickly for effective disinfection in a vented system, introducing such a catalyst into a closed system has been found to offer improved disinfection possibilities not otherwise available. Specifically, larger catalysts provide a higher initial rate of activity which, in turn, delivers a quicker pressure rise to high hydrostatic pressure within the system. A larger catalyst provides for an increased surface area to fluid volume ratio, thereby providing a larger catalyst that is more effective in bringing end reaction concentrations to lower, ocularly safe levels.

Figure 5:
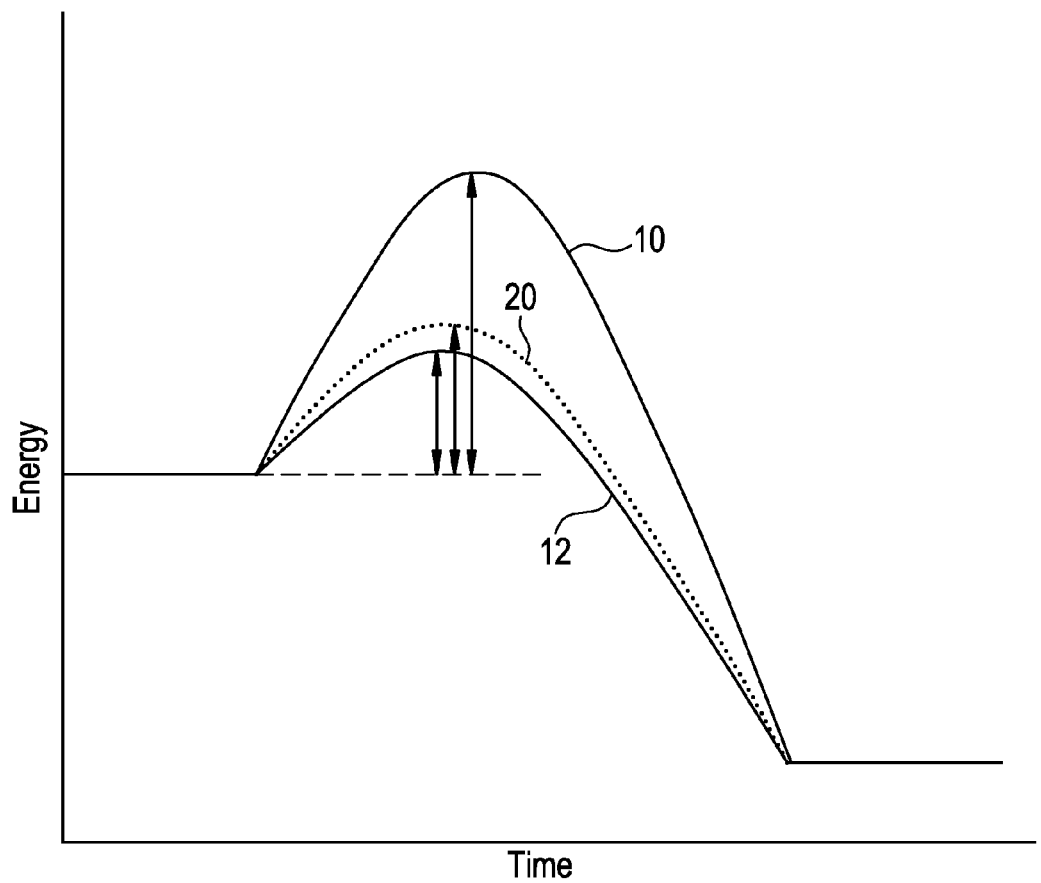
FIG. 5 is a graph which is similar to the graph shown FIG. 1, but which also plots the energy associated with activating at an elevated pressure.

High hydrostatic pressure resulting from containment of evolving oxygen also increases the amount of dissolved oxygen that can be absorbed within the solution allowing it to become saturated with the gas. For example, at 300 p.s.i. and 23 degrees Celsius, approximately 0.0122 milliliters of oxygen dissolve into a 10 milliliter solution bath. FIG. 5 provides a graph which not only compares the energy associated with activating without a catalyst (line 10) to the energy associated with activating with a catalyst (line 12), but also plots the energy associated with activating at an elevated pressure (line 20).

As initially high hydrostatic pressure tends to slow the reaction by raising the level of activation energy required for decomposition, oxygen dissolving into instead of rising from the solution plays a part as well. Viewed strictly from a mechanical perspective, although diffusion ultimately will balance the concentration of solution within a container over time, hydrogen peroxide has been found to be subject to short term stratification within a solution bath when decomposition is initiated by a catalytic structure and those oxygen molecules not entering into solution under pressure form bubbles of much smaller size leading to decreased mechanical mixing of the solution bath as they rise to the surface.

Additive effects to enhance the disinfection process are therefore available when energy and byproducts yielded by the disproportionation reaction are harnessed and incorporated back into the process. Increased hydrostatic pressure created by expanding oxygen within the disinfecting chamber allows more evolved oxygen to dissolve into solution. As a result, less mixing occurs from increasingly smaller and fewer rising gas bubbles, and the activation energy requirement for decomposition increases. This works to retard the rate at which decomposition occurs in order to sustain a significantly higher concentration of solution for a longer period of time. FIG. 6 compares peroxide concentration as it changes over time, in a vented system (i.e., under typical atmospheric conditions) (line 22) versus a high pressure system (i.e., under typical atmospheric conditions) (line 24). As shown, under elevated pressure the peroxide concentration is 2.4 times that of the vented system at 5 minutes into the reaction (i.e., after 5 minutes of elapsed reaction time), 4.7 times that of the vented system at 10 minutes, 6.8 times that of the vented system at 20 minutes, and 6.4 times that of the vented system at 30 minutes.

When employing high pressure from contained, expanding, evolved oxygen in order to assist a hydrogen peroxide solution in obtaining greater penetration and oxidative potential, the high hydrostatic pressure conditions thereby created can also be leveraged to exploit the natural dynamic equilibrium of pathogens, as diffusion allows for an elevated oxygen condition to be created within the organism under oxygen saturated conditions sustained by the pressurized solution bath. A further additive effect can thereafter be realized as a consequence of introducing a subsequent rapid decompression from the high pressure condition to elicit release of dissolved oxygen from solution observable as an effervescence of the gas, and thereby cause expansion of excess absorbed oxygen within the pathogen to further stress the organism's cell membrane undergoing oxidative denaturation from hydrogen peroxide exposure. This mechanism compliments the destructive effects of oxidative denaturation upon the pathogen's proteins. Following decompression, with high pressure having been relieved, the catalytic reaction is therefore allowed to resume at a faster, low pressure pace in order to assure that decomposition has been completed to an acceptable level within the desired 6 to 8 hour time span.

FIGS. 7 and 8 illustrate a contact lens disinfecting system 40, wherein the system is in accordance with an embodiment of the present invention, and is configured to create the desirable elevated pressure, oxygen saturation and sustained peroxide concentration conditions within its contact lens holding and reaction chamber, in order to enhance disinfection by additive effect as disclosed hereinabove.

As shown in FIGS. 7 and 8, the contact lens disinfecting system 40 comprises a cup 42 and a cap assembly 44 which is configured to threadably engage the top 46 of the cup 42. The cup 42 is conventional in that it is generally cylindrical and provides a reaction chamber 48 therein for disinfecting contact lenses.

The cap assembly 44 includes a valve body 50, and a stem 52 is attached to and hermetically sealed to the valve body 50. A catalyst 54 (conventional with regard to composition), sized to complete the reaction within an appropriate time, is affixed to the bottom 56 of the stem 52. Additionally, contact lens retaining baskets 58 are disposed on the stem 52. The retaining baskets 58 are configured to pivot open and closed, in order to receive contact lenses, and maintain the contact lenses in a space 60 which is provided between the stem 52 and the retaining baskets 58. The stem 52 and retaining baskets 58 may be conventional, such as described in either U.S. Pat. No. 4,200,187 or U.S. Pat. No. 4,750,610, both of which are incorporated herein by reference in their entirety. A sealing member 62 is provided on the stem 52, for sealing against an internal wall 64 of the cup 42.

As discussed, the cap assembly 44 includes a valve body 50. The valve body 50 preferably consists of a single, multi-walled body such as is indicated in FIGS. 7 and 8, and is configured to threadably engage the top 46 of the cup 42. The valve body 50 provides a passage 66, an aperture 68 leads to the passage 66, and a breathable membrane 70 is provided at the end 72 of the passage 66, on the valve body 50. The breathable membrane 70 may be composed of, for example, either a filter material or a hydrophobic filtering material having a pore size of preferably one half micron but no more than two microns.

The valve body 50 also includes a receptacle 74 which has a plunger 76 disposed therein. The plunger 76 can take many forms, but one preferred structure of the plunger 76 provides that the plunger 76 consists of a plastic body having a piston 78, formed of an elastomeric material, molded onto the end of the plastic body. As such, the piston 78 effectively defines the end 80 of the plunger 76. The plunger 76 is configured to traverse within the receptacle 74 of the valve body 50, such that the piston 78 can traverse relative to a piston cylinder area 82.

The piston 78 is configured to provide a first plunger seal 84 and a second plunger seal 86. When the plunger 76 is in the position shown in FIG. 7, the first and second plunger seals 84, 86 seal against respective internal walls 88, 90 of the valve body 50, thereby providing that the system 40 is sealed. However, when the plunger 76 moves to the position shown in FIG. 8, the first plunger seal 84 slides out of contact with the internal wall 88 of the valve body 50 (in the piston cylinder area 82), thereby providing that the reaction chamber 48 can vent, as will be described in more detail later hereinbelow.

In use, approximately 10 milliliters of hydrogen peroxide solution 92 is poured into the cup 42, the retaining baskets 58 on the stem 52 are pivoted open, contact lenses are placed onto the stem 52, and then the retaining baskets 58 are pivoted closed in order to retain the contact lenses in space 60. Finally, the stem 52 is inserted into the cup 42, and the cap assembly 44 is threaded onto the top 46 of the cup 42. Preferably, the cup 42 is sized such that when the cap assembly 44 is threaded onto the top 46 of the cup 42, with 10 milliliters of hydrogen peroxide 92 being contained in the cup 42, there remains 4 cc's of headspace 98 above the hydrogen peroxide 92, for containment of oxygen gas which evolves during the disinfection process. While providing 4 cc's of headspace is one possibility, the volume of the headspace 98 can be varied as can the surface area of the catalyst 54, in order to achieve a desired internal pressure to control the reaction as previously discussed.

The catalytically-stimulated disproportionation reaction begins when contact lenses, contained within space 60 between the stem 52 and retaining baskets 58, are immersed in the hydrogen peroxide solution 92 simultaneously with introduction of the catalyst 54 into the hydrogen peroxide solution 92. Thereafter, disinfection solution and pressure within the system is contained between the cup 42 and the cap assembly 44 via the sealing member 62 being sealed against the internal wall 64 of the cup 42, and via the first plunger seal 84 being sealed against wall 88, as shown in FIG. 7.

A detent ball 100 is contained in the valve body 50 and is biased into contact with the plunger 76 by a spring member 102. Specifically, when the plunger 76 is in the sealing position as shown in FIG. 7, the detent ball 100 engages a receiving groove 104 which is provided on the plunger 76. From a starting position as shown in FIG. 7, longitudinal movement of the plunger 76 within the receptacle 74 is controlled by the detent ball 100 residing within the receiving groove 104 of the plunger 76. The detent ball 100 is held against the plunger 76 by the spring element member 102 which is appropriately configured to detain its movement until sufficient force is exerted upon piston 78 (in the direction of arrow 106 in FIG. 7) to push the detent ball 100 aside, allowing the plunger 76 to traverse within the receptacle 74 from the position shown in FIG. 7 to the position shown in FIG. 8. Although a ball-shaped detent is shown in FIGS. 7 and 8, a similar function could be achieved using a detent which is shaped differently than a ball, such as an elongated-shaped detent. Regardless, the detent 100 functions to provide that the plunger 76 can move from its sealing position shown in FIG. 7, to its venting position shown in FIG. 8, only upon the reaction chamber 46 reaching a substantial high pressure condition. When the plunger 76 is in the position shown in FIG. 7, the plunger seal 84 effectively contains the evolved gas and prevents it from passing upward the along plunger 76. Once the pressure in the reaction chamber 46 increases to a sufficient level, the plunger 76 moves upward in the receptacle 74 as shown in FIG. 8, allowing the reaction chamber 46 to vent.

In addition to including the valve body 50, the cap assembly 44 also includes a cap 108 which is engaged with the valve body 50. The cap 108 is generally cylindrical and retains the valve body 50 via, for example, a circumferential lip 110. Specifically, the cap 108 is mounted on the valve body 50 such that the cap 108 is rotatable relative to the valve body 50. This will be described more fully later hereinbelow. Regardless, the cap 108 has a post 112 therein, and longitudinal motion of the plunger 76 within the receptacle 74 is limited by a top 114 of the plunger 76 contacting the post 112, as shown in FIG. 8.

Once the piston 78 has moved sufficiently within the piston cylinder area 82, the piston 78 enters a transition section 116. The transition section 116 is configured to gradually reduce seal contact of the plunger seal 84 against the internal wall 88 of the piston cylinder area 82, and therefore initiates both leakage of oxygen gas from within the headspace 98 and effervescence of dissolved oxygen into headspace 98, past the piston 78, into the transition section 116, through the aperture 68 into passage 66, through the breathable membrane 70, into the atmosphere. This fluid path is indicated with arrows 118 in FIG. 8.

As described above, the breathable membrane 70 may be composed of either a filter material or a hydrophobic filtering material having a pore size of preferably one half micron but no more than two microns. Although not essential to the reaction of the peroxide, the breathable membrane 70 provides a barrier to entrance of undesirable organisms after the peroxide solution 92 has been catalytically decomposed.

Figure 9:
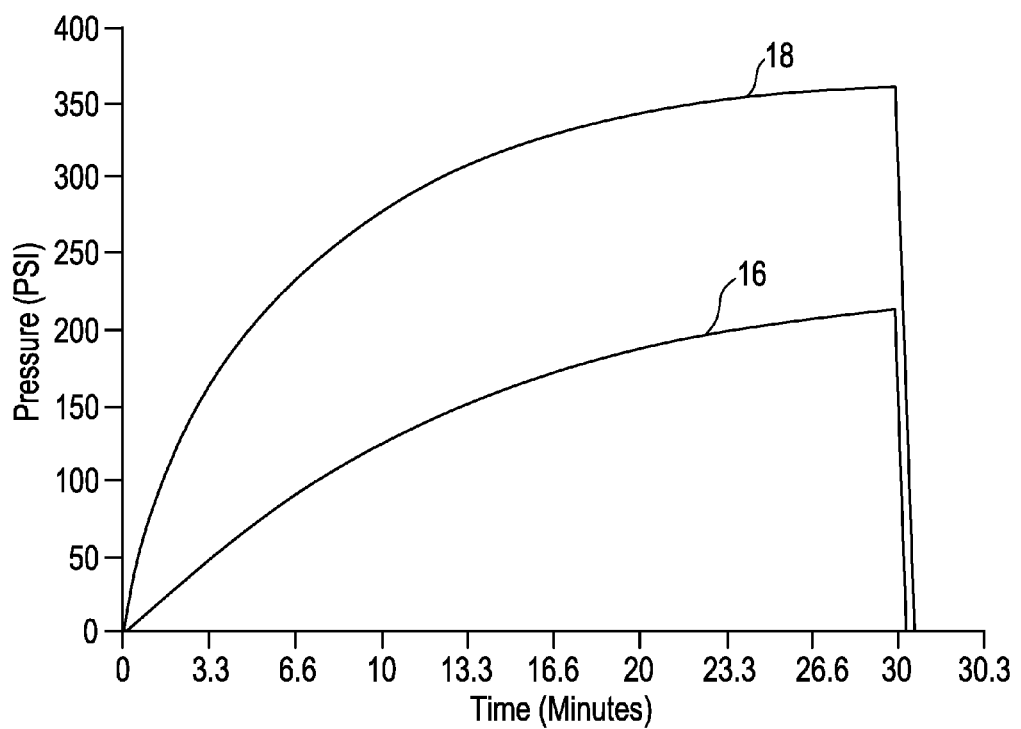
FIG. 9 is a graph which is similar to the graph shown in FIG. 4, but goes on to show the pressure decreasing once venting occurs.

Decompression provides a further additive effect to the disinfection process when oxygen occupying the headspace 98 is allowed to escape by movement of the piston 78 and saturated oxygen within the hydrogen peroxide disinfection solution effervesces from it, thereby allowing pressure in the headspace 98 to drop to a point slightly above the atmospheric ambient much more quickly than a pathogenic organism could adjust to maintain dynamic equilibrium. During the pressurization and decompression phases of the process, including venting to atmosphere, pressure within the headspace 98 rises and falls in a manner as shown in FIG. 9 (depending on which size catalyst 54 is used, wherein as discussed above in connection with FIG. 4, the curve identified with reference numeral 16 relates to the use of a catalyst having a given surface area, and the curve identified with reference numeral 18 relates to the use of a catalyst having twice the surface area). After high pressure has been relieved within the system 40, the rate of catalytically-inspired disproportionation of the hydrogen peroxide solution 92 increases beyond that just prior to pressure relief as the activation energy level is lowered. Mixing currents are also generated as oxygen boils from the solution 92, and these resulting currents initially speed the catalytic decomposition by disturbing stratification to bring more peroxide molecules into contact with the catalyst 54. Oxygen continues to be evolved as final decomposition of the solution 92 lowers peroxide concentration toward an ocularly safe level for use of the lenses disinfected within.

As discussed above, the cap 108 is mounted on the valve body 50 such that the cap 108 is rotatable relative to the valve body 50. As shown in FIGS. 7 and 8, preferably the upper surface 120 of the valve body 50 provides a castellated structure 122 which is configured to mate with corresponding castellated structure 124 which is provided inside the cap 108. A spring element 126 is preferably provided inside the cap assembly 44, between the cap 108 and the valve body 50. Specifically, one end 128 of the spring element 126 preferably engages a shoulder 130 which is provided on the valve body 50, and the other end 132 of the spring element 126 preferably engages an inside surface 134 of the cap 108. As such, the castellated structure 124 which is provided inside the cap 108 is biased (via the spring element 126) out of engagement with the corresponding castellated structure 122 which is provided on the top surface 120 of the valve body 50.

Once the disinfection process has been completed, after 6 to 8 hours for example, the cap 108 which is ordinarily free to rotate relative to the valve body 50, must be pressed downward to compress the spring element 126, in order to engage the castellated structure 124 on the inside surface 134 of the cap 108 with the castellated structure 122 on valve body 50. Once the cap 108 is pressed down such that the two castellated structures 122, 124 are engaged with each other, rotation of the cap 108 in a counter-clockwise direction causes the cap assembly 44 to unscrew from its threaded engagement with the top 46 of the cup 42.

Pushing the cap 108 downward to unscrew the cap assembly 44 also causes the post 112 of the cap 108 to push down on the plunger 76, causing the plunger 76 to shift downward in the receptacle 74, and allowing the detent ball 100 to re-engage the receiving groove 104 of the plunger 76. The translation of the plunger 76 downward also causes the piston seal 84 to re-seal with the internal wall 88 of the piston cylinder area 82. As such, the device 40 is thereafter prepared for the next disinfection process.

Preferably, sufficient threads 136, 138 are provided on the cup 42 and the cap assembly 44, respectively, to allow the sealing member 62 on the stem 52 to pass a chamfer 140 which is provided at the top 46 of the cup 42, in order to relieve any residual pressure that may be present prior to final unscrewing of the cap assembly 44 from the cup 42. Conversely, during installation of the cap assembly 44, sufficient thread engagement is provided before the sealing member 62 on the stem 52 passes below the chamfer 140, in order to assure that adequate structure is engaged for containment of pressure generated during disinfection.

Pressing the cap 108 down upon the valve body 50 to re-engage the mating castellation structures 122, 124 for installation of the cap assembly 44 to the cup 42, as would be done by a user to initiate the next disinfection cycle, also serves to assure that the plunger 76 reseats into its proper position before the next cycle is started. Upon threading the cap assembly 44 onto the cup 42, and upon releasing the cap 108, the system arrives at the condition shown in FIG. 7, ready for the next disinfection cycle.

As discussed, the contact lens disinfecting system 40 shown in FIGS. 7 and 8 is configured to enhance the disinfection process by additive effect. Of course, other embodiments (such as embodiments employing other cap assembly designs, for example) are entirely possible in order to implement the additive affect enhanced disinfection process described hereinabove.

Figure 10:
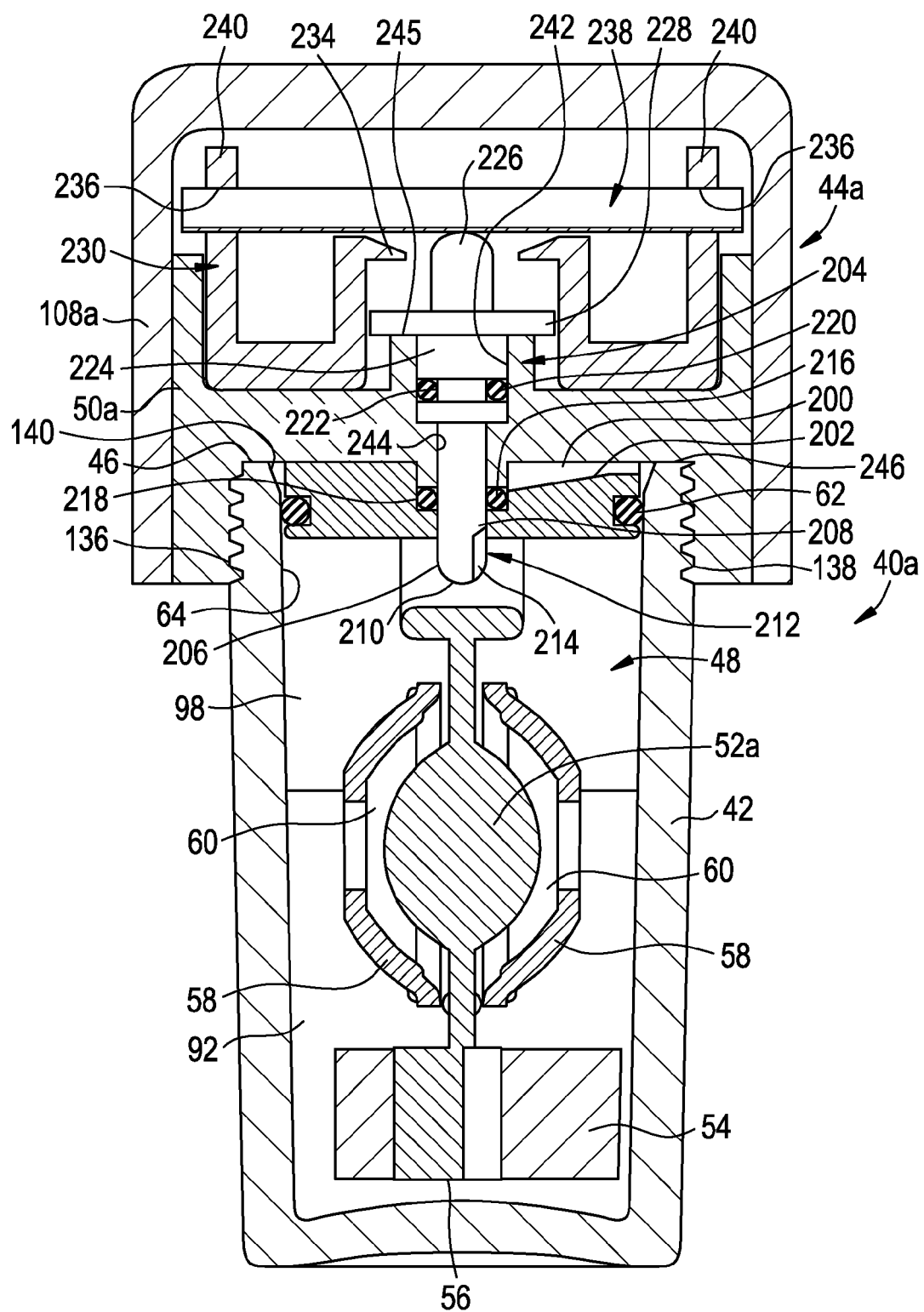
FIGS. 10 and 11 are cross-sectional views of a contact lens disinfecting system which is in accordance with an alternative embodiment of the present invention.
Figure 11:
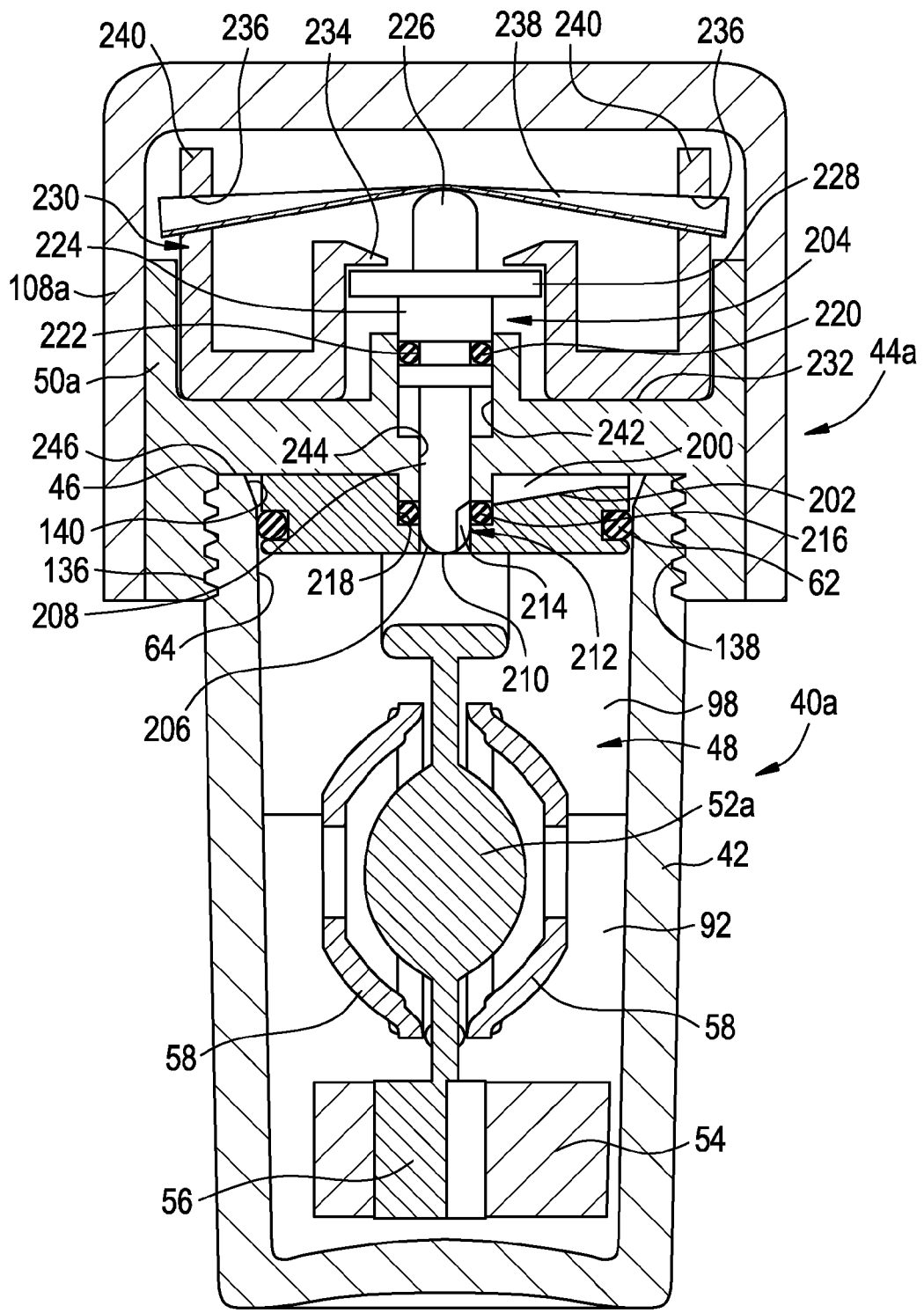

For example, FIGS. 10 and 11 are cross-sectional views of a contact lens disinfecting system 40a which is in accordance with an alternative embodiment of the present invention. Like the contact lens disinfection system 40 shown in FIGS. 7 and 8, the contact lens disinfection system 40a shown in FIGS. 10 and 11 is configured to create the desirable elevated pressure, oxygen saturation and sustained peroxide concentration conditions within its contact lens holding and reaction chamber, in order to enhance disinfection by additive effect as disclosed hereinabove.

The structure and operation of the contact lens disinfection system 40a shown in FIGS. 10 and 11 is similar to the contact lens disinfecting system 40 shown in FIGS. 7 and 8 in many respects. As such, identical reference numerals are used to identify identical parts. For example, much like the contact lens disinfecting system 40 shown in FIGS. 7 and 8, the contact lens disinfection system 40a shown in FIGS. 10 and 11 includes a cup 42 and a cap assembly 44a which is configured to threadably engage the top 46 of the cup 42, and the cup 42 is conventional in that it is generally cylindrical and provides a reaction chamber 48 therein for disinfecting contact lenses.

The cap assembly 44a comprises a cap 108a which is affixed to a valve body 50a. The valve body 50a is configured to threadably engage the top 46 of the cup 42, and a stem 52a is attached to and hermetically sealed to the valve body 50a. A catalyst 54 (conventional with regard to composition), sized to complete the reaction within an appropriate time, is affixed to the bottom 56 of the stem 52a. Additionally, contact lens retaining baskets 58 are disposed on the stem 52a. The retaining baskets 58 are configured to pivot open and closed, in order to receive contact lenses, and maintain the contact lenses in a space 60 which is provided between the stem 52a and the retaining baskets 58. A sealing member 62 is provided on the stem 52a, for sealing against an internal wall 64 of the cup 42.

As described above, the contact lens disinfecting system 40 shown in FIGS. 7 and 8 provides that there is a passage 66 in the valve body 50, and an aperture 68 leads to the passage 66, to provide a fluid path for venting. In contrast, the contact lens disinfecting system 40a shown in FIGS. 10 and 11 provides a fluid passage 200 between a top 202 of the stem 52a and the valve body 50a.

The cap assembly 44a includes a plunger 204, and a bottom part 206 of the plunger 204 defines a piston 208. The piston 208 may be generally cylindrical having a domed end surface 210. The piston 208 includes a venting feature 212, such as a longitudinal slot 214 along the piston 208. While a longitudinal slot 214 is shown in FIGS. 10 and 11, the venting feature 212 may take other forms, such as a flat along the side of the piston 208, or a reduced diameter section along the piston 208, for example. Regardless, the venting feature 212 provides for communication with the passage 200 for venting the reaction chamber 48, as will be described more fully later hereinbelow.

A piston seal 216 is provided in a receiving groove 218 between the stem 52a and the valve body 50a, and a plunger seal 220 is provided in a receiving groove 222 which is on a cylindrical portion 224 of the plunger 204. Both seals 216, 220 are preferably formed of a suitable elastomeric material. The plunger 204 also preferably includes a domed top portion 226 and a flange 228. As will be described more fully later hereinbelow, the plunger 204 is configured to traverse up and down relative to the valve body 50a, to facilitate venting and sealing, respectively, of the reaction chamber 48 in the cup 42.

Figure 12:
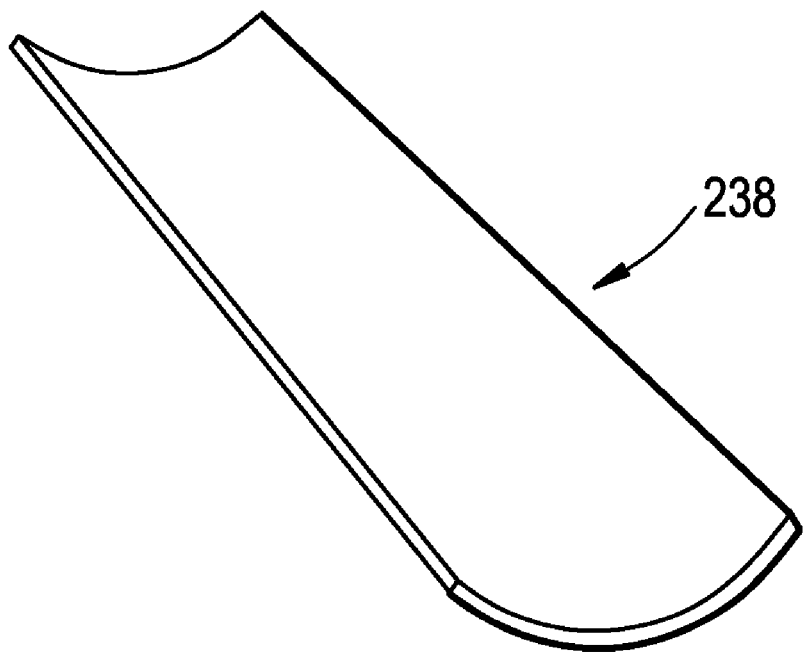
FIG. 12 is a perspective view of a spring member component of the contact lens disinfecting system shown in FIGS. 10 and 11.

The cap assembly 44a also includes a spring-retaining member 230 which is affixed to an inside, top surface 232 of the valve body 50a, between the valve body 50a and the cap 108a. Preferably, the spring-retaining member 230 is a single piece, multi-walled structure. The spring-retaining member 230 preferably includes inwardly-extending flanges 234 which function as a plunger stop, via contact with the flange 228 on the plunger 204, as shown in FIG. 11. The spring-retaining member 230 also includes apertures 236 for receiving a control spring 238, and control spring supports 240. As shown in FIG. 12, preferably the control spring 238 is a beam-like member having a generally U-shaped cross-section, and acts as a beam to transfer the pressure induced load from the abutting plunger 204 to the control spring supports 240, thereby resisting upward movement of the plunger 204. While FIG. 12 illustrates a specific control spring configuration, the control spring make take other forms. Regardless, the spring-retaining member 230 retains the control spring 238 in its apertures 236, and the control spring 238 works to effectively control the up and down movement of the plunger 204. Specifically, while the cylindrical portion 224 of the plunger 204 traverses in a plunger cylinder area 242 in the valve body 50a, the piston 208 traverses in a piston cylinder area 244 in the valve body 50a. Initially, the contact lens disinfecting system 40a appears as shown in FIG. 10, with the plunger 204 in the down position. In the down position, the flange 228 of the plunger 204 contacts surface 245 of the valve body 50a, which restricts further downward travel of the plunger 204.

Much like as with the contact lens disinfecting system 40 shown in FIGS. 7 and 8, the contact lens disinfection system 40a shown in FIGS. 10 and 11 provides that in use, approximately 10 milliliters of hydrogen peroxide solution 92 is poured into the cup 42, the retaining baskets 58 on the stem 52a are pivoted open, contact lenses are placed onto the stem 52a, and then the retaining baskets 58 are pivoted closed in order to retain the contact lenses in space 60. Finally, the stem 52a is inserted into the cup 42, and the cap assembly 44a is threaded onto the top 46 of the cup 42. Preferably, the cup 42 is sized such that when the cap assembly 44a is threaded onto the top 46 of the cup 42, with 10 milliliters of hydrogen peroxide 92 being contained in the cup 42, there remains 4 cc's of headspace 98 above the hydrogen peroxide 92, for containment of oxygen gas which evolves during the disinfection process. While providing 4 cc's of headspace is one possibility, the volume of the headspace 98 can be varied as can the surface area of the catalyst 54, in order to achieve a desired internal pressure to control the reaction as previously discussed.

Figure 13:
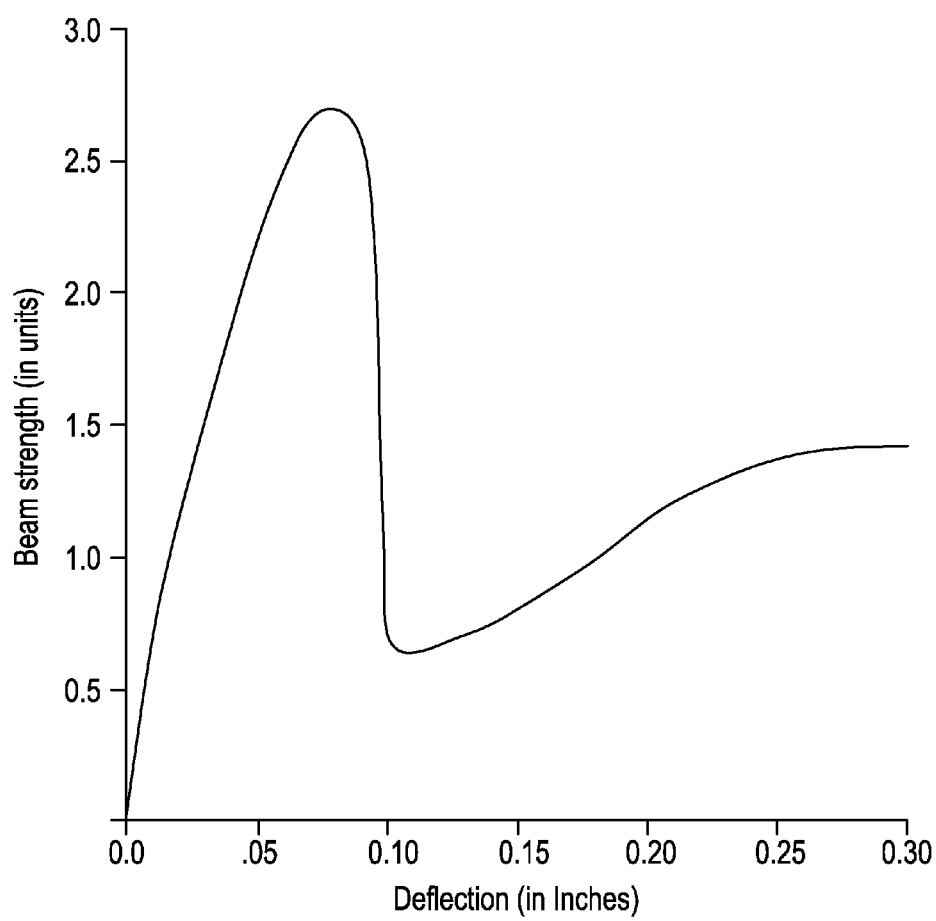
FIG. 13 is a graph which shows how the beam strength of the spring member of FIGS. 10-12 changes based on the amount of deflection.

Once the catalyst 54 has been introduced to the hydrogen peroxide solution 92, and the contact lens disinfecting system 40a is sealed by threading the cap assembly 44a onto the top 46 of the cup 42, the system 40a appears as shown in FIG. 10, and pressure in the reaction chamber 48 starts to increase. As pressure with the headspace 98 against the piston 208 continues to increase from the ongoing disproportionation and the plunger 204 traverses (upward) in response, the "U" shape of the control spring 238 deforms in a manner in which the cross-sectional height of the "U" form becomes smaller and the beam strength of the control spring 238 declines. When the combination of the force delivered to the control spring 238 by the plunger 204 reaches the maximum beam strength of the control spring 238, the control spring 238 flattens and buckles, allowing the plunger 204 (and piston 208) to move upward until the flange 228 on the plunger 204 abuts the plunger stop 234, as shown in FIG. 11. In this deformed condition, the control spring 238 offers the plunger 204 significantly lower resistance. Typical resistance to the bending force offered by the control spring 238 can more clearly be understood by viewing FIG. 13. FIG. 13 is a graph which shows how the beam strength of a spring, such as the control spring 238, changes based on the amount of deflection. As shown in FIG. 13, the control spring 238 demonstrates its maximum beam strength of 2.69 units when the plunger 204 bearing upon it reaches 0.090 inches of travel and its minimum beam strength of 0.64 units (or less than 25% of the maximum) at 0.105 inches of plunger travel (i.e., just 0.025 inches later).

Movement of the plunger 204 upward to the plunger stop 234 allows the venting feature 212 on the piston 208 to pass beyond the piston seal 216, thereby providing an avenue of escape for the pressurized oxygen within the headspace 98. Escaping oxygen flowing along venting feature 212 is allowed to pass above the piston seal 216, flow into passage 200, and slowly escape along the close-fitting, but unsealed, interface between the rim 246 of the cup 42 and the valve body 50a, and between mating faces of threads 136, 138 provided on cup 42 and the cap assembly 44a, respectively. These unsealed interfaces allow gas flow into the ambience and although inhibiting flow rate, impose no pressure limitation upon the escaping gas. Gas pressure traveling along the venting feature 212 on the piston 208 also passes along the clearance between the piston 208 and the valve body 50a, thereby impinging upon the plunger seal 220. Because the plunger seal 220 is larger in diameter, force exerted by the plunger 204 against the plunger stop 234 and the control spring 238 increases beyond that exerted by the piston 208 and remains greater until the slowly dissipating gas pressure within the headspace 98 has reduced sufficiently for the control spring 238 to overcome the force of the plunger 204 and drive the plunger 204 downward causing the venting feature 212 on the piston 208 to pass below the piston seal 216, as shown in FIG. 10, thereby terminating communication between the headspace 98 and the ambience.

Figure 14:
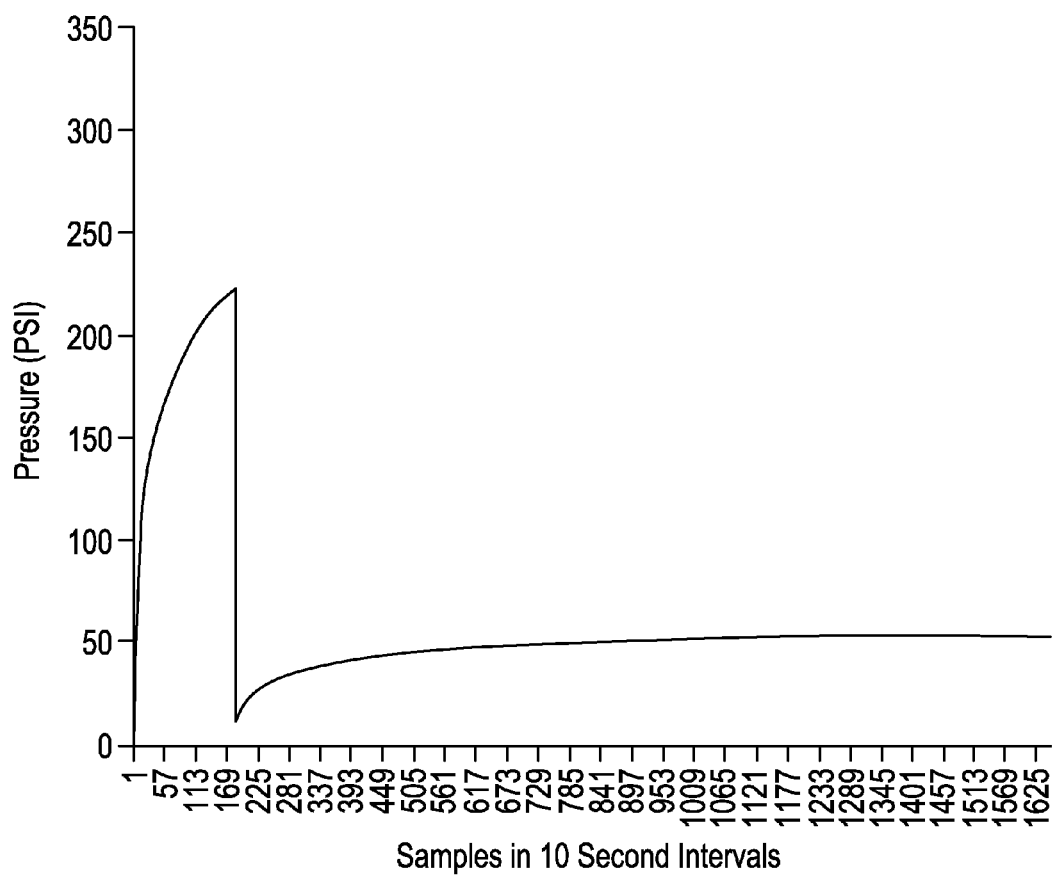
FIG. 14 is a graph which shows the change in pressure over time during the disinfection process, when the contact lens disinfecting system shown in FIGS. 10 and 11 is used.

As shown in FIG. 14, applying the example of a spring (i.e., control spring 238) functioning as shown in FIG. 13 and a receiving force from the piston 208 of a 0.0123 square inch area, allows a peak pressure of 219 p.s.i. to be achieved within headspace 98 before the control spring 238 deflects sufficiently to allow venting, as shown in FIG. 11. A plunger seal 220 having twice the diameter of the piston 208 would present a 0.049 square inch surface area and provide sufficient force to keep the control spring 238 deflected until residual pressure within the headspace 98 drops to approximately 13 p.s.i, at which point the control spring 238 straightens, pushing the plunger 204 (and piston 208) back down, reseating it against surface 245, as shown in FIG. 10.

Following venting of headspace 98 as described above, activity of the pressure-inhibited catalytic reaction increases and then declines as the conversion of hydrogen peroxide into water and oxygen depletes the peroxide supply at a decreasing rate. Residual pressure after the plunger 204 and piston 208 have reseated (as shown in FIG. 10), combined with pressure resulting from the breakdown of remaining hydrogen peroxide, elevates the pressure within headspace 98 in a manner as shown in FIG. 14, as the disinfection process completes 6 to 8 hours after starting.

Much like the contact lens disinfecting system 40 shown in FIGS. 7 and 8, the contact lens disinfecting system 40a shown in FIGS. 10 and 11 preferably provides that sufficient threads 136, 138 are provided on the cup 42 and the cap assembly 44a, respectively, to allow the sealing member 62 on the stem 52a to pass a chamfer 140 which is provided at the top 46 of the cup 42, in order to relieve any residual pressure that may be present prior to final unscrewing of the cap assembly 44a from the cup 42. Conversely, during installation of the cap assembly 44a, sufficient thread engagement is provided before the sealing member 62 on the stem 52a passes below the chamfer 140, in order to assure that adequate structure is engaged for containment of pressure generated during disinfection.

Figure 15:
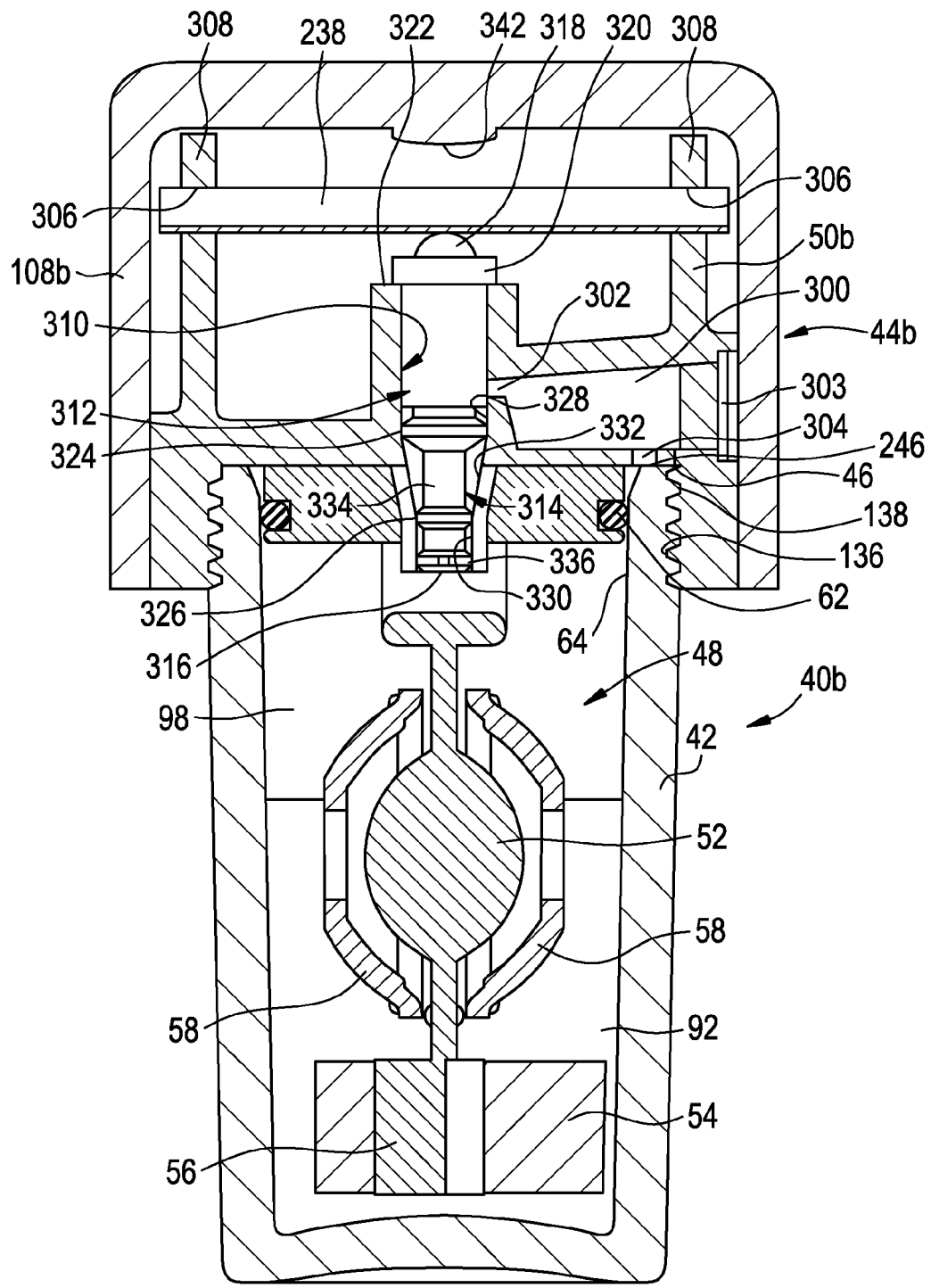
FIGS. 15 and 16 are cross-sectional views of a contact lens disinfecting system which is in accordance with yet another embodiment of the present invention.
Figure 16:
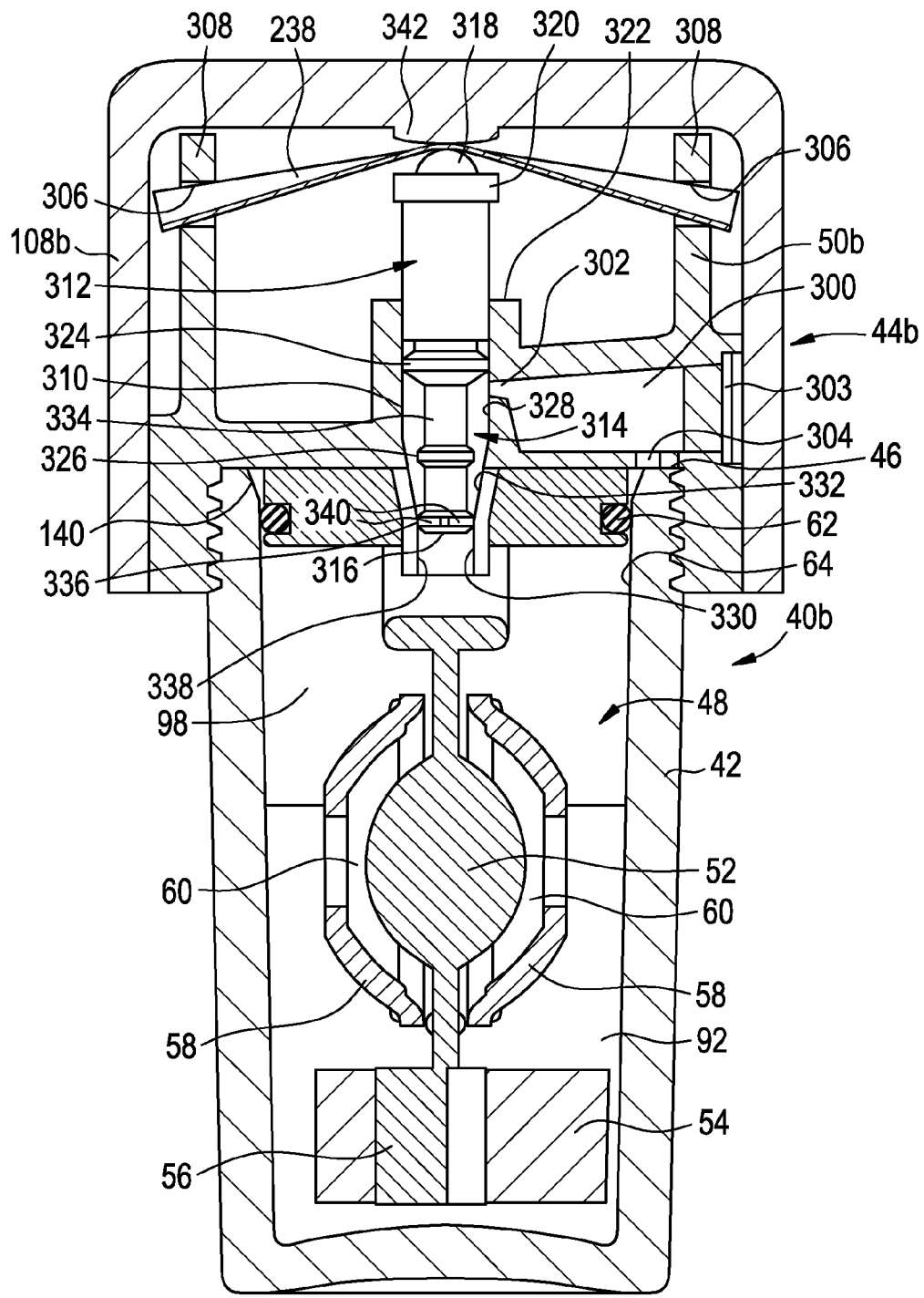

FIGS. 15 and 16 are cross-sectional views of a contact lens disinfecting system 40b which is in accordance with yet another embodiment of the present invention. The system 40b is also configured to create the desirable elevated pressure, oxygen saturation and sustained peroxide concentration conditions within its contact lens holding and reaction chamber, in order to enhance disinfection by additive effect as disclosed hereinabove. In many respects, the structure and operation of the contact lens disinfection system 40b shown in FIGS. 15 and 16 is similar to the contact lens disinfecting systems 40, 40a previously described. As such, identical reference numerals are used to identify identical parts. For example, much like the contact lens disinfecting systems 40, 40a, the contact lens disinfection system 40b includes a cup 42 and a cap assembly 44b which is configured to threadably engage the top 46 of the cup 42, and the cup 42 is conventional in that it is generally cylindrical and provides a reaction chamber 48 therein for disinfecting contact lenses.

The cap assembly 44b comprises a cap 108b which is affixed to a valve body 50b. The valve body 50b is preferably a single piece, multi-walled structure and is configured to threadably engage the top 46 of the cup 42. A stem 52 is attached to and hermetically sealed to the valve body 50b. A catalyst 54 (conventional with regard to composition), sized to complete the reaction within an appropriate time, is affixed to the bottom 56 of the stem 52. Additionally, contact lens retaining baskets 58 are disposed on the stem 52. The retaining baskets 58 are configured to pivot open and closed, in order to receive contact lenses, and maintain the contact lenses in a space 60 which is provided between the stem 52 and the retaining baskets 58. A sealing member 62 is provided on the stem 52, for sealing against an internal wall 64 of the cup 42.

Much like contact lens disinfecting system 40, contact lens disinfecting system 40b provides that there is a passage 300 in the valve body 50b, and that an aperture 302 leads to the passage 300, to provide a fluid path for venting the reaction chamber 48. There is a plug 303 at the end of the passage 300, and the plug 303 seals the end of the passage as well as provides a barrier to entrance of undesirable organisms after the peroxide solution 92 has been catalytically decomposed. The valve body 50b also has an additional aperture 304, i.e., an exhaust port, which allows venting gas to travel from the passage 300, to the rim 246 of the cup 42, along the threads 136, 138 between the cup 42 and the cap assembly 44b, and out to the atmosphere. The plug 303 works to contain the pressure in the passage 300, limiting the escape of venting gas out through the exhaust port 304 and along the threads 136, 138.

Apertures 306 are provided on the valve body 50b for retaining a control spring 238 proximate spring supports 308 (said control spring preferably being identical in nature to the control spring of the system 40a shown in FIGS. 10 and 11). The valve body 50b includes a plunger receptacle 310, and a plunger 312 is disposed in the plunger receptacle 310. The plunger 312 can take many forms, but one preferred structure of the plunger 312 provides that the plunger 312 consists of a plastic body having a piston 314, formed of an elastomeric material, molded onto the plastic body to provide a plunger seal 324 and a piston seal 326.

The plunger 312 preferably has a domed-shaped top surface 318 and a flange 320. The plunger 312 is configured to traverse within the receptacle 310 of the valve body 50b, and the flange 320 is configured to limit downward movement of the plunger 312 in the receptacle 310, via contact between the flange 320 and surface 322 of the valve body 50b as shown in FIG. 15.

The plunger 312 also defines a plunger seal 324, and a piston seal 326 is provided on the piston 314. When the plunger 312 traverses in the receptacle 310, the plunger seal 324 traverses relative to a plunger cylinder area 328 of the receptacle 310, and the piston seal 326 traverses relative to a piston cylinder area 330 of the receptacle 310. A transition area 332 is provided between the plunger cylinder area 328 and the piston cylinder area 330, and the plunger 312 has a plunger stem 334 which is located between the piston seal 326 and the plunger seal 324. At the end 316 of the plunger 312 is a plunger guide 336, and the plunger guide 336 is configured to contact an internal wall 338 of the valve body 50b, in the piston cylinder area 330, and align the piston 314.

Much like as with the contact lens disinfecting systems 40, 40a, the contact lens disinfection system 40b shown in FIGS. 15 and 16 provides that in use, approximately 10 milliliters of hydrogen peroxide solution 92 is poured into the cup 42, the retaining baskets 58 on the stem 52 are pivoted open, contact lenses are placed onto the stem 52, and then the retaining baskets 58 are pivoted closed in order to retain the contact lenses in space 60. Finally, the stem 52 is inserted into the cup 42, and the cap assembly 44b is threaded onto the top 46 of the cup 42. Preferably, the cup 42 is sized such that when the cap assembly 44b is threaded onto the top 46 of the cup 42, with 10 milliliters of hydrogen peroxide 92 being contained in the cup 42, there remains 4 cc's of headspace 98 above the hydrogen peroxide 92, for containment of oxygen gas which evolves during the disinfection process. While providing 4 cc's of headspace is one possibility, the volume of the headspace 98 can be varied as can the surface area of the catalyst 54, in order to achieve a desired internal pressure to control the reaction as previously discussed.

Once the catalyst 54 has been introduced to the hydrogen peroxide solution 92, and the contact lens disinfecting system 40b is sealed by threading the cap assembly 44b onto the top 46 of the cup 42, the system 40b appears as shown in FIG. 15, and pressure in the reaction chamber 48 starts to increase. From the starting position shown in FIG. 15, longitudinal movement of the plunger 312 traversing within the valve body 50b is limited by the control spring 238, which is configured to detain the plunger's movement until pressure within headspace 98 enters the piston cylinder area 330 and bears upon the piston 314 with sufficient force to exceed the beam strength of control spring 238 and thereby initiate its flattening and buckling. As this deformation of the control spring 238 occurs, piston 314 exits piston cylinder area 330 and traverses into the transition area 332. The plunger stem tip 334 remains engaged with the internal wall 338 of the valve body 50b in the piston cylinder area 330 in order to stabilize the plunger 312.

Preferably, one or more flats 340 (or other structure) are provided on the plunger stem tip 334, to allow for the flow of pressurized oxygen from headspace 98 to enter plunger cylinder area 328 through the transition section 332, and bear next upon the larger diameter plunger seal 324 to provide additional force against control spring 238, thereby forcing it against a stop boss 342 (see FIG. 16) which is provided on the underside of the cap 108b. As the plunger seal 324 rises in response to the gas pressure it is receiving, it uncovers aperture 302, allowing gas under pressure to enter passageway 300 and communicate with exhaust port 304, positioned directly over the rim 246 of the cup 42.

Gas exiting the exhaust port 304 impinges upon and flows along the unsealed, closely-abutting surfaces of the rim 246 of the cup 42 and the valve body 50b, where it is distributed around the rim 246 of cup 42 and subsequently flows to atmosphere along the mating clearance of the threads 136, 138 into the ambiance. Although inhibiting flow rate, these unsealed surfaces encountered by the escaping gas impose no pressure limitation upon it. Once the pressure in the reaction chamber 48 has sufficiently decreased, as a result of venting, the control spring 238 pushes the plunger 312 down and re-sets the system 40b, as shown in FIG. 15.

Much like contact lens disinfecting systems 40, 40a, the contact lens disinfecting system 40b shown in FIGS. 15 and 16 preferably provides that sufficient threads 136, 138 are provided on the cup 42 and the cap assembly 44b, respectively, to allow the sealing member 62 on the stem 52 to pass a chamfer 140 which is provided at the top 46 of the cup 42, in order to relieve any residual pressure that may be present prior to final unscrewing of the cap assembly 44b from the cup 42. Conversely, during installation of the cap assembly 44b, sufficient thread engagement is provided before the sealing member 62 on the stem 52 passes below the chamfer 140, in order to assure that adequate structure is engaged for containment of pressure generated during disinfection.

Figure 17:
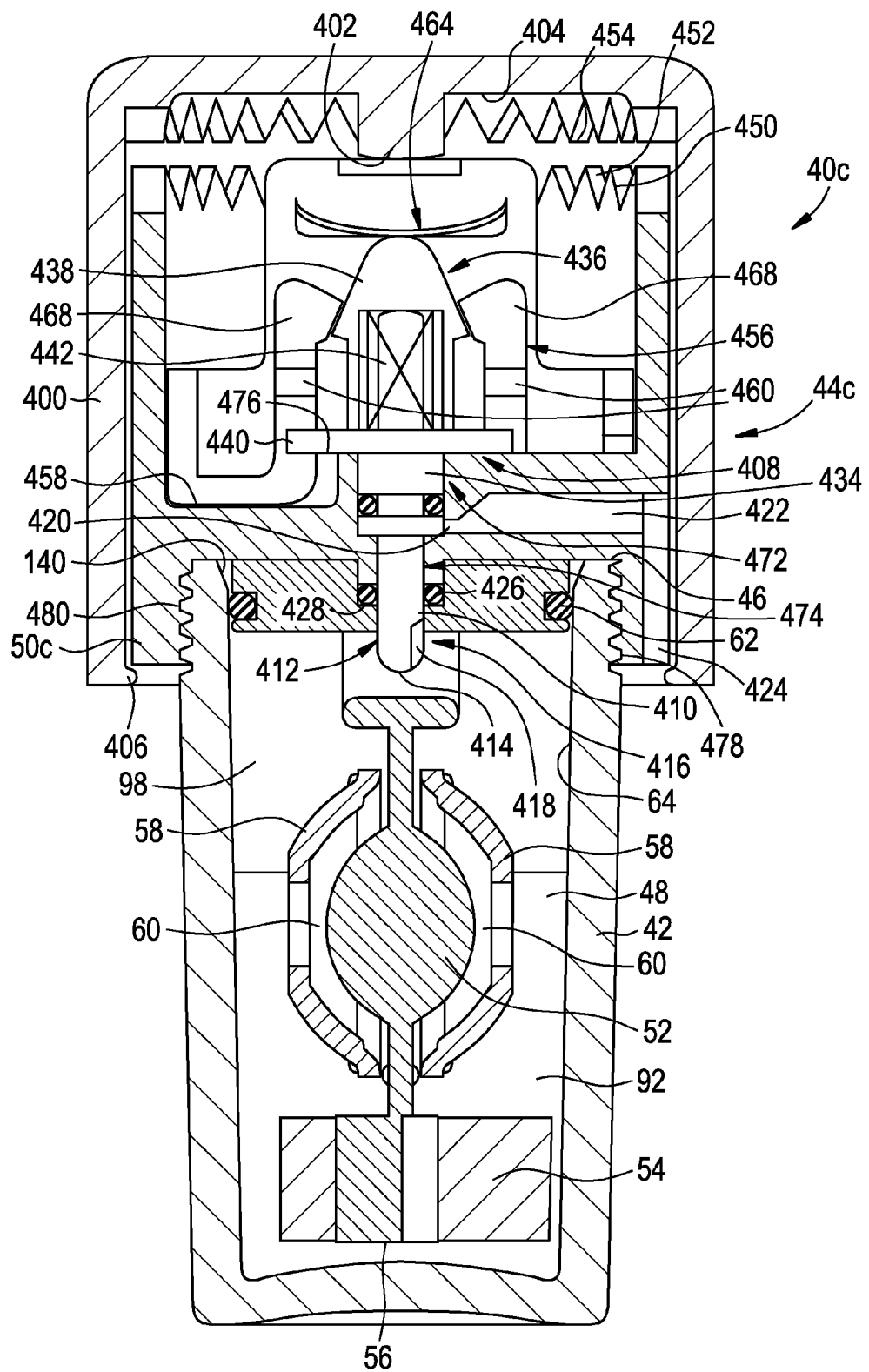
FIGS. 17 and 18 are cross-sectional views of a contact lens disinfecting system which is in accordance with another embodiment of the present invention.
Figure 18:
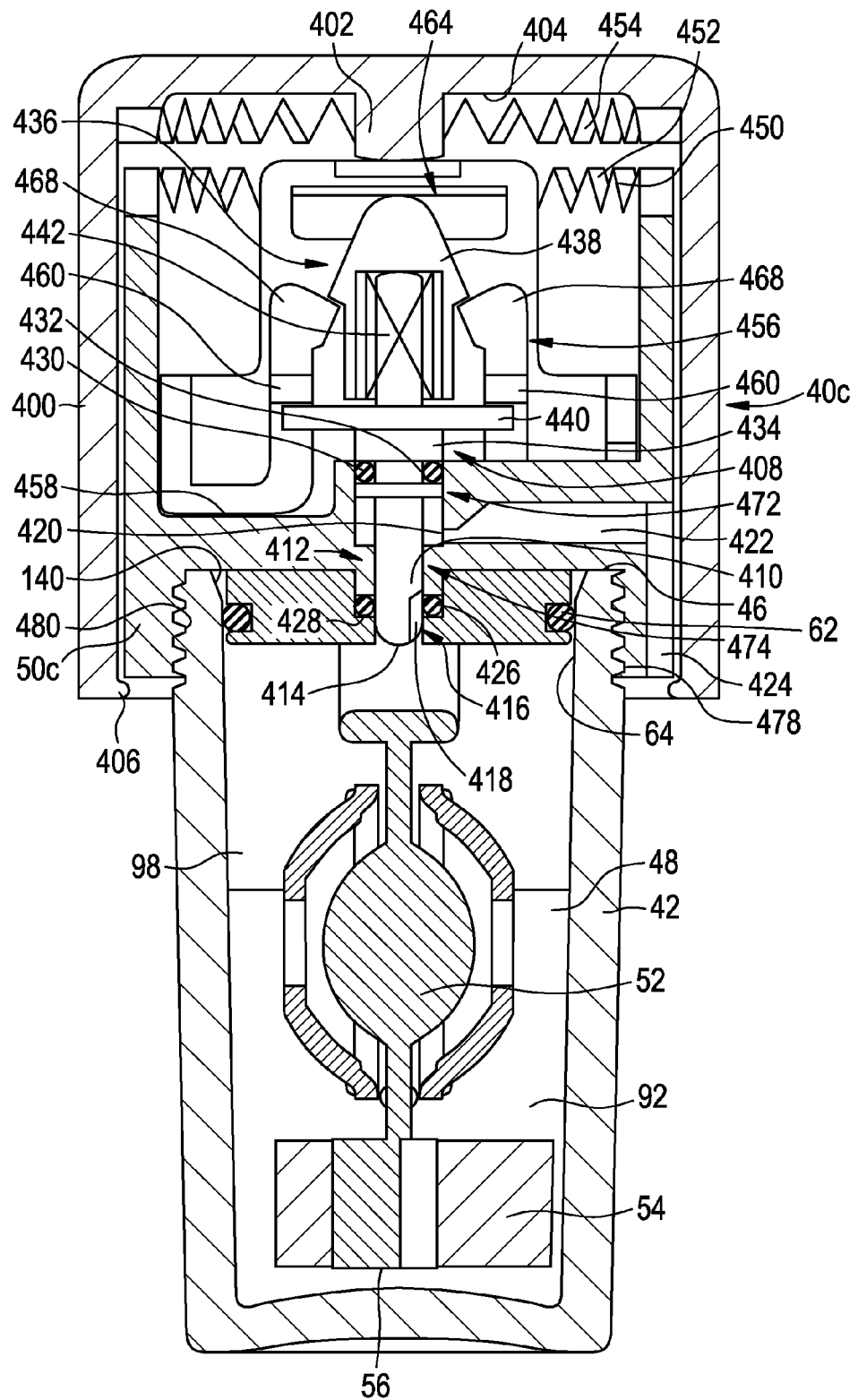

FIGS. 17 and 18 are cross-sectional views of a contact lens disinfecting system 40c which is in accordance with yet another embodiment of the present invention. The system 40c is also configured to create the desirable elevated pressure, oxygen saturation and sustained peroxide concentration conditions within its contact lens holding and reaction chamber, in order to enhance disinfection by additive effect as disclosed hereinabove. In many respects, the structure and operation of the contact lens disinfection system 40c shown in FIGS. 17 and 18 is similar to the contact lens disinfecting systems 40, 40a and 40b previously described. As such, identical reference numerals are used to identify identical parts. For example, much like the contact lens disinfecting systems 40, 40a, 40b the contact lens disinfection system 40c includes a cup 42 and a cap assembly 44c which is configured to threadably engage the top 46 of the cup 42, and the cup 42 is conventional in that it is generally cylindrical and provides a reaction chamber 48 therein for disinfecting contact lenses.

The cap assembly 44c comprises a cap 400 which is affixed to a valve body 50c. The cap 400 has a post 402 which is disposed on an inside surface 404 of the cap 400, and has a circumferential lip 406 which tends to keep the cap 400 retained on the valve body 50c.

The valve body 50c is preferably a single piece, multi-walled structure and is configured to threadably engage the top 46 of the cup 42. A stem 52 is attached to and hermetically sealed to the valve body 50c. A catalyst 54 (conventional with regard to composition), sized to complete the reaction within an appropriate time, is affixed to the bottom 56 of the stem 52. Additionally, contact lens retaining baskets 58 are disposed on the stem 52. The retaining baskets 58 are configured to pivot open and closed, in order to receive contact lenses, and maintain the contact lenses in a space 60 which is provided between the stem 52 and the retaining baskets 58. A sealing member 62 is provided on the stem 52, for sealing against an internal wall 64 of the cup 42.

Much like as with the contact lens disinfecting systems 40, 40a, 40b previously described, the contact lens disinfection system 40c shown in FIGS. 17 and 18 provides that in use, approximately 10 milliliters of hydrogen peroxide solution 92 is poured into the cup 42, the retaining baskets 58 on the stem 52 are pivoted open, contact lenses are placed onto the stem 52, and then the retaining baskets 58 are pivoted closed in order to retain the contact lenses in space 60. Finally, the stem 52 is inserted into the cup 42, and the cap assembly 44c is threaded onto the top 46 of the cup 42. Preferably, the cup 42 is sized such that when the cap assembly 44c is threaded onto the top 46 of the cup 42, with 10 milliliters of hydrogen peroxide 92 being contained in the cup 42, there remains 4 cc's of headspace 98 above the hydrogen peroxide 92, for containment of oxygen gas which evolves during the disinfection process. While providing 4 cc's of headspace is one possibility, the volume of the headspace 98 can be varied as can the surface area of the catalyst 54, in order to achieve a desired internal pressure to control the reaction as previously discussed.

The cap assembly 44c includes a plunger 408, and a bottom part 410 of the plunger 408 defines a piston 412. The piston 412 may be generally cylindrical having a domed end surface 414. The piston 412 includes a venting feature 416, such as a longitudinal slot 418 along the piston 412. While a longitudinal slot 418 is shown in FIGS. 17-20, the venting feature 416 may take other forms, such as a flat along the side of the piston 412, or a reduced diameter section along the piston 412, for example. Regardless, the venting feature 416 provides for communication with a vent port 420 and ultimately a passage 422 in the valve body 50c for venting the reaction chamber 48 along an opening 424 between the cap 400 and the valve body 50c, as will be described more fully later hereinbelow.

A piston seal 426 is provided in a receiving groove 428 between the stem 52 and the valve body 50c, and a plunger seal 430 is provided in a receiving groove 432 which is on a cylindrical portion 434 of the plunger 408. Both seals 426, 430 are preferably formed of a suitable elastomeric material. The plunger 408 also preferably has a plunger cap 436 disposed thereon, and the plunger cap 436 provides a domed top portion 438 and the plunger 408 provides a flange 440. The plunger 408 also includes an upwardly-extending post 442 which is received in a receptacle 446 in the plunger cap 436, and a plunger cap spring 448 is disposed in the receptacle 446. As will be described more fully later hereinbelow, the plunger 408 is configured to traverse up and down relative to the valve body 50c, to facilitate venting and sealing, respectively, of the reaction chamber 48 in the cup 42.

Figure 19:
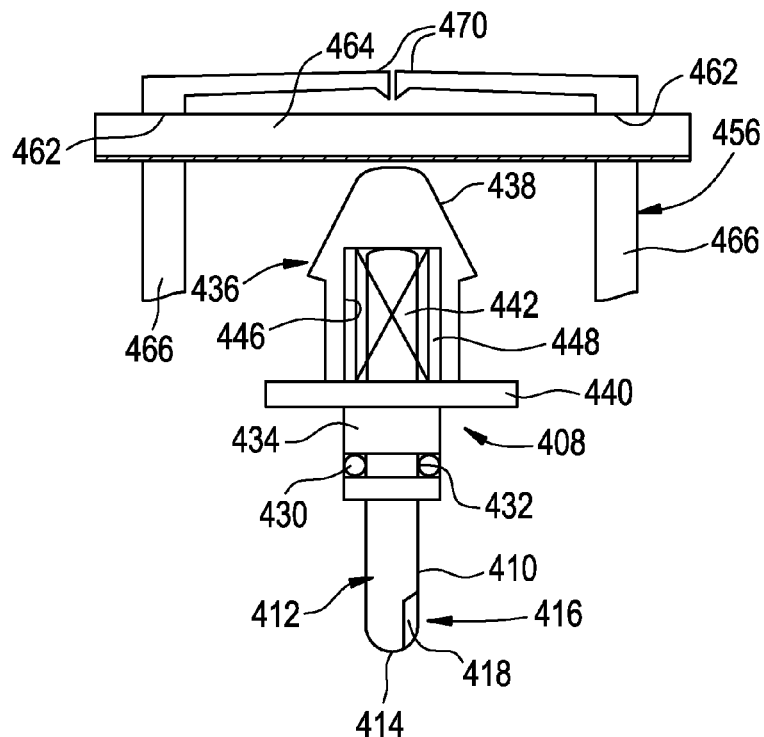
FIGS. 19 and 20 are side cross-sectional views of a portion of the contact lens disinfecting system which is shown in FIGS. 17 and 18.
Figure 20:
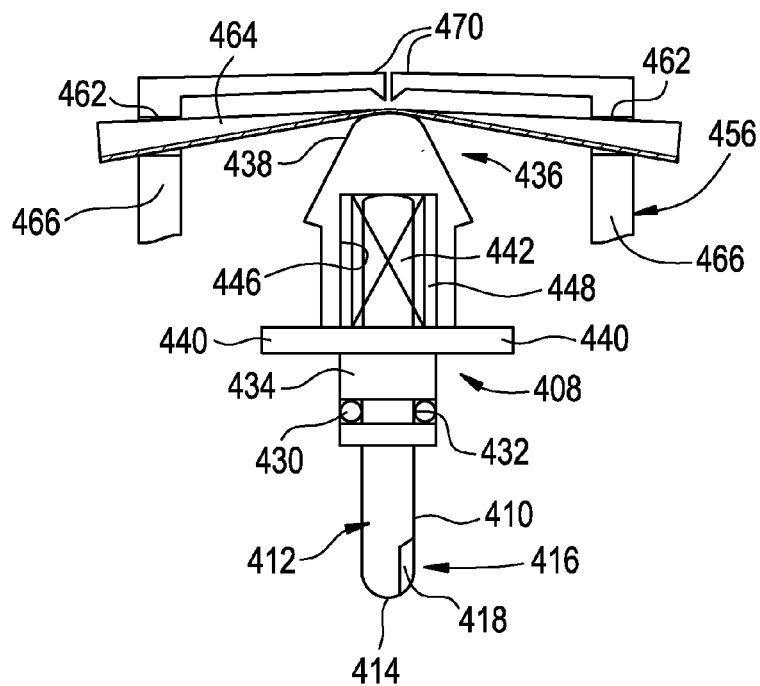

As shown in FIGS. 17 and 18, preferably the upper surface 450 of the valve body 50c provides a castellated structure 452 which is configured to mate with corresponding castellated structure 454 which is provided inside the cap 400. A spring-retaining member 456 is affixed to an inside, top surface 458 of the valve body 50c, between the valve body 50c and the cap 400. Preferably, the spring-retaining member 456 is a single piece, multi-walled structure. The spring-retaining member 456 preferably includes inwardly-extending stops 460 which function as a plunger stop, via contact with the flange 440 on the plunger 408, as shown in FIG. 18. As shown in FIGS. 19 and 20, the spring-retaining member 456 also includes apertures 462 for receiving a control spring 464, control spring supports 466, and cap return spring structures 470, as will be described in more detail later hereinbelow. The spring-retaining member 456 also includes deflectable latching members 468 which are configured to spread apart and allow the plunger cap 436 to pass (see FIG. 18).

The control spring 464 is preferably much like the control spring 238 which is included in contact lens disinfecting systems 40a and 40b (see FIGS. 10-16, as well as the associated description hereinabove). As such, the control spring 464 is preferably a beam-like member having a generally U-shaped cross-section, and acts as a beam to transfer the pressure induced load from the abutting plunger 408 to the control spring supports 466, thereby resisting upward movement of the plunger 408. The spring-retaining member 456 retains the control spring 464 in its apertures 462 (see FIGS. 19 and 20), and the control spring 464 works to effectively control the up and down movement of the plunger 408. Specifically, while the cylindrical portion 434 of the plunger 408 traverses in a plunger cylinder area 472 in the valve body 50c, the piston 412 traverses in a piston cylinder area 474 in the valve body 50c. Initially, the contact lens disinfecting system 40c appears as shown in FIG. 17, with the plunger 408 in the down position. In the down position, the flange 440 of the plunger 408 contacts surface 476 of the valve body 50c, which restricts further downward travel of the plunger 408.

Figure 21:
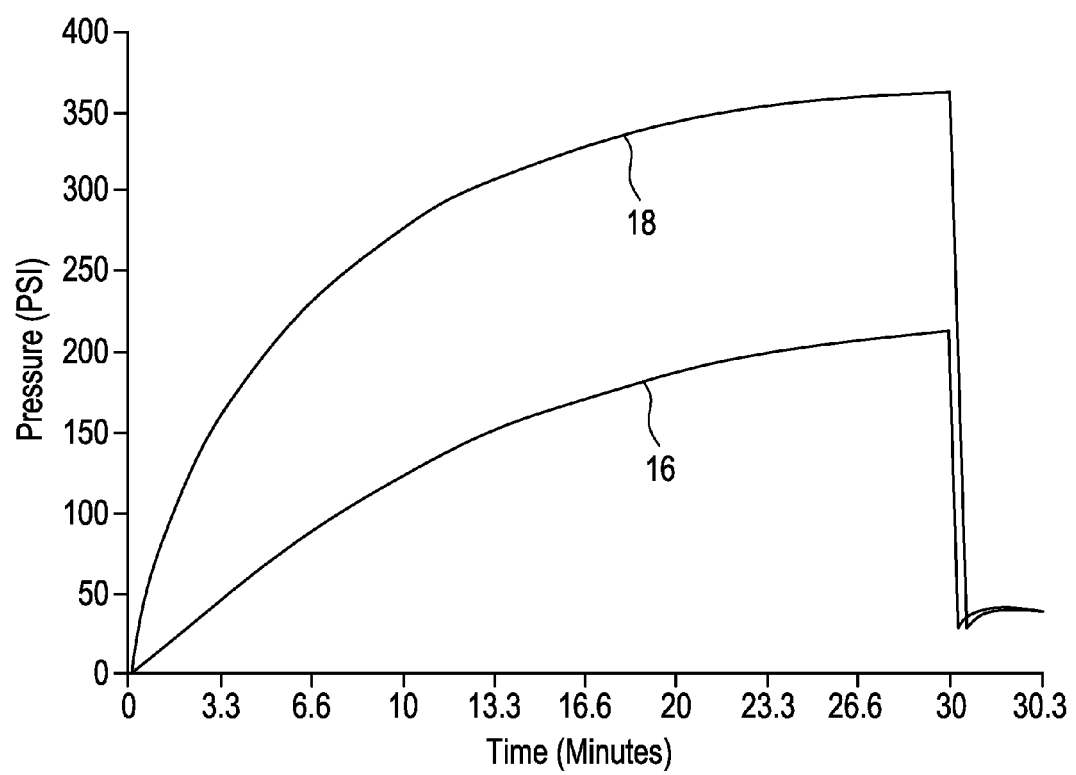
FIG. 21 is a graph which shows the change in pressure over time during the disinfection process, when the contact lens disinfecting system shown in FIGS. 17 and 18 is used.

As mentioned above, control spring 464 acts as a beam to transfer the pressure-induced load from abutting plunger 408 to control spring supports 466 (see FIGS. 17 and 19), thereby resisting upward movement of the plunger 408 (and plunger cap 436). As pressure within the headspace 98 against piston 412 from the ongoing disproportionation rises to the desirable 180 p.s.i. to 366 p.s.i., the plunger 408 (with plunger cap 436) gains sufficient force to overcome control spring 464. In response, the "U" shape of control spring 464 begins to deform in a manner in which the cross-sectional height of the "U" form becomes smaller causing the beam strength of control spring 464 to decline. When force delivered by plunger 408 reaches the maximum beam strength of control spring 464, the spring 464 flattens and buckles as its cross-section diminishes thereby allowing plunger 408 (with piston 412 and plunger cap 436) to move upward as shown in FIGS. 18 and 20 until flange 440 abuts plunger stops 460 affixed to valve body 50c, arresting any further upward movement of plunger 408. In this deformed condition, control spring 464 offers plunger 408 significantly lower resistance. A typical shape transition in response to bending loads by a spring such as control spring 464 illustrated in FIGS. 19 and 20 and the spring's resistance forces during such a transition in shape can more clearly be understood by viewing FIG. 13. The control spring 464 shown in FIGS. 17-20 demonstrates its maximum beam strength of 2.69 units when the plunger 408 bearing upon it reaches 0.090 inch of travel and its minimum beam strength of 0.64 units, or less than 25% of the maximum, at 0.105 inch of plunger travel just 0.025 of an inch later. Movement of piston 412 drives plunger 408 upward and flange 440 toward plunger stops 460 allowing the leading edge of the venting feature 416 to pass beyond piston seal 426, as shown in FIG. 18, thereby providing an avenue of escape for the pressurized oxygen within the headspace 98 and initiating depressurization within the disinfection system 40c (FIG. 21). Specifically, pressurized oxygen gas leaving headspace 98 and entering plunger cylinder area 472 is stopped by plunger seal 430 and is then forced to enter vent port 420 where it is directed into the ambience through passageway 422 (and opening 424).

Coincident with the upward movement of plunger 408, as flange 440 approaches stops 460, the upwardly driven plunger cap 436 forces deflectable latching members 468 to spread apart and allow plunger cap 436 to bypass. When the latching members 468 then return to their original position, the plunger cap 436 becomes trapped above, as shown in FIG. 18, thereby retaining control spring 464 in its deflected condition (as shown in FIGS. 18 and 20). Plunger cap spring 448 then provides the only downward force against plunger 408. A small force from the plunger cap spring 448, in the range of 0.12 lb-0.50 lb in the immediate example herein, is sufficient to drive plunger 408 (with piston 412) back downward once pressure within headspace 98 has dissipated to a range of 9.8 p.s.i. to 40 p.s.i., for example. Downward movement of piston 412 allows the leading edge of the venting feature 416 to pass below piston seal 426 thereby terminating communication between headspace 98 and the ambience, as shown in FIG. 17. Following venting of headspace 98 as described above, activity of the pressure-inhibited catalytic reaction initially increases and then decreases as the conversion of hydrogen peroxide into water and oxygen depletes the peroxide supply at a decreasing rate. As pressure within headspace 98 begins to climb in response to the invigorated catalytic reaction, pressure against piston 412 causes plunger 408 to compress plunger cap spring 448 sufficiently to allow enough movement for venting feature 416 to move past piston seal 426 and allow pressure to escape headspace 98. After pressure in headspace 98 has again vented off, force from spring 464 bearing on plunger 408 pushes plunger 408 (and piston 412) downward along piston seal 426, terminating flow through venting feature 416. This venting cycle of low pressure inspired opening and closing continues, keeping pressure within headspace 98 low, limiting communication between headspace 98 and the ambience to an outward flow condition while oxygen gas continues to be liberated through disproportionation of the hydrogen peroxide within cup 42 until an ocularly safe peroxide concentration level has been reached after 6 to 8 hours of reaction time.

Once the disinfection process has been completed, after 6 to 8 hours for example, the freely rotating cap 400 retained to valve body 50c by lip 406, must be pressed downward in order to engage the castellated structure 452 on the cap 400 with corresponding castellated structure 454 on the valve body 50c, in order to allow unthreading of the cap assembly 44c from its threaded engagement with the top 46 of the cup 42, for retrieval of the disinfected contact lenses. The act of pressing down on the cap 400 also allows the post 402 in the cap 400 to deflect the cap return spring structures 470, which extend from the control spring supports 466, downward against control spring 464 which in turn pushes the plunger cap 436 against the latching members 468. This action causes the latching members 468 to deflect outward in response to downward pressure against the plunger cap 436, allowing passage therethrough of the plunger cap 436, and further driving the plunger 408 to its original seated position, as shown in FIG. 17, whereupon plunger cap 436 again becomes captured by the now overhanging latching members 468 as they spring back into place. The downward pressing action required to remove the cap assembly 44c from the top 46 of the cup 42 and to replace it therefore serves to reset the pressure control mechanism contained within in preparation for the next disinfection cycle. Much like with the other systems 40, 40a, 40b previously described, preferably sufficient threads 478, 480 are provided on the cup 42 and the cap assembly 44c, respectively, to allow the sealing member 62 on the stem 52 to pass a chamfer 140 which is provided at the top 46 of the cup 42, in order to relieve any residual pressure that may be present prior to final unscrewing of the cap assembly 44c from the cup 42. Conversely, during installation of the cap assembly 44c, sufficient thread engagement is provided before the sealing member 62 on the stem 52 passes below the chamfer 140, in order to assure that adequate structure is engaged for containment of pressure generated during disinfection.

FIG. 21 is a graph which indicates how the pressure in the cup 42 changes over time (depending on which size catalyst 54 is used, wherein the curve identified with reference numeral 16 relates to the use of a catalyst having a given surface area, and the curve identified with reference numeral 18 relates to the use of a catalyst having twice the surface area) when the disinfection system 40c shown in FIGS. 17 and 18 is employed. As shown in FIG. 21, the system 40c provides that during the pressurization and decompression phases of the process including venting to atmosphere, pressure within headspace 98 initially rises (i.e., to the high pressure level established by the control spring 464), and then drops precipitously during venting after which it rises and falls slightly (i.e., as it responds to low pressure control provided by the interaction of plunger 408 and plunger cap spring 448). Concurrent with initial high pressure relief, the rate of catalytically-inspired disproportionation of hydrogen peroxide solution 92 within the cup 42 increases beyond that just prior to pressure relief as the activation energy level is lowered. Mixing currents are also generated as oxygen boils from solution 92 and these resulting currents initially speed the catalytic decomposition by disturbing stratification to bring more peroxide molecules into contact with the catalyst 54. Oxygen continues to evolve into the headspace 98 and is controlled by the cyclic venting previously described as final decomposition of the solution lowers peroxide concentration toward an ocularly safe level for use of the lenses disinfected within.

Figure 22:
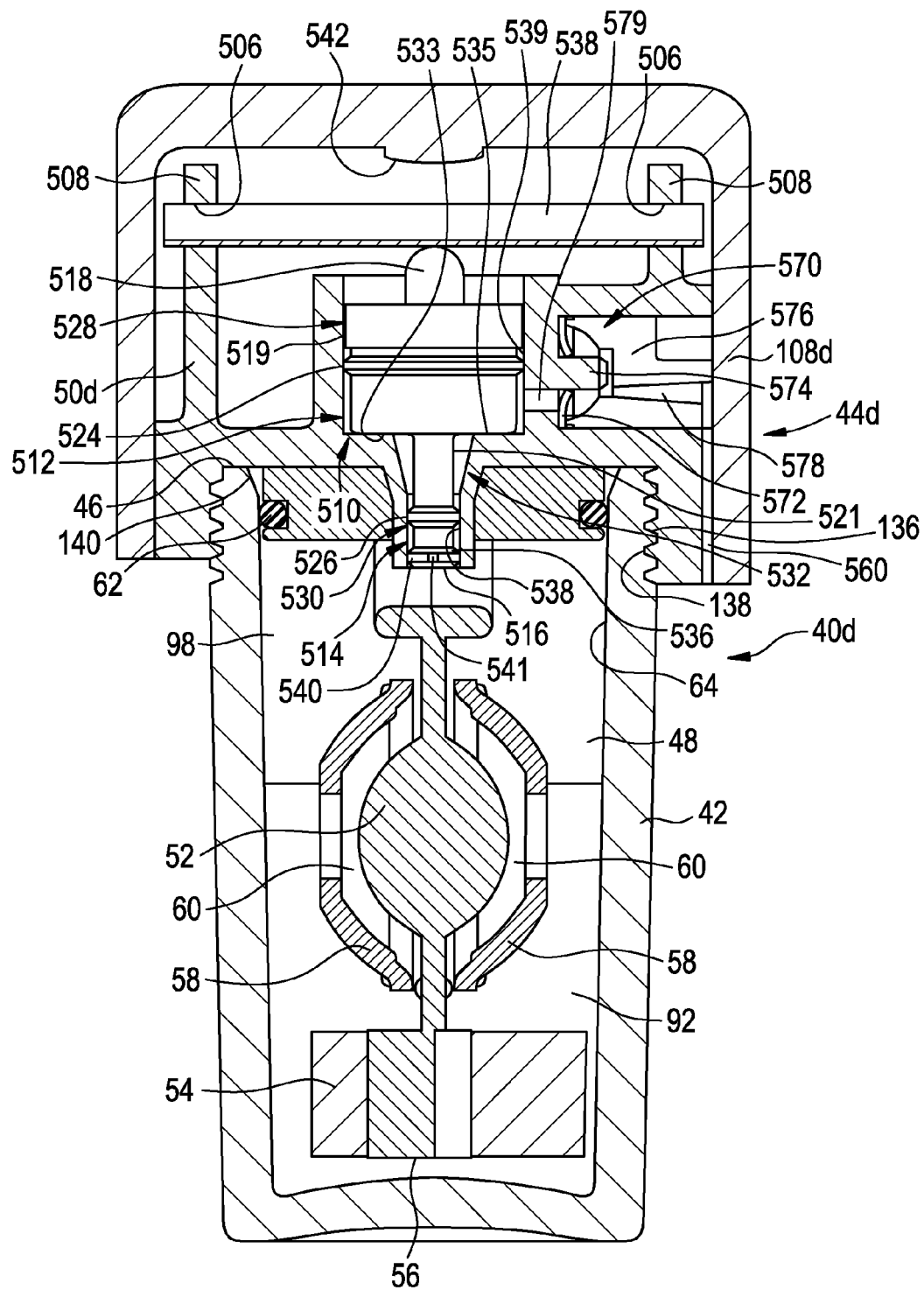
FIGS. 22 and 23 are cross-sectional views of a contact lens disinfecting system which is in accordance with another embodiment of the present invention.
Figure 23:
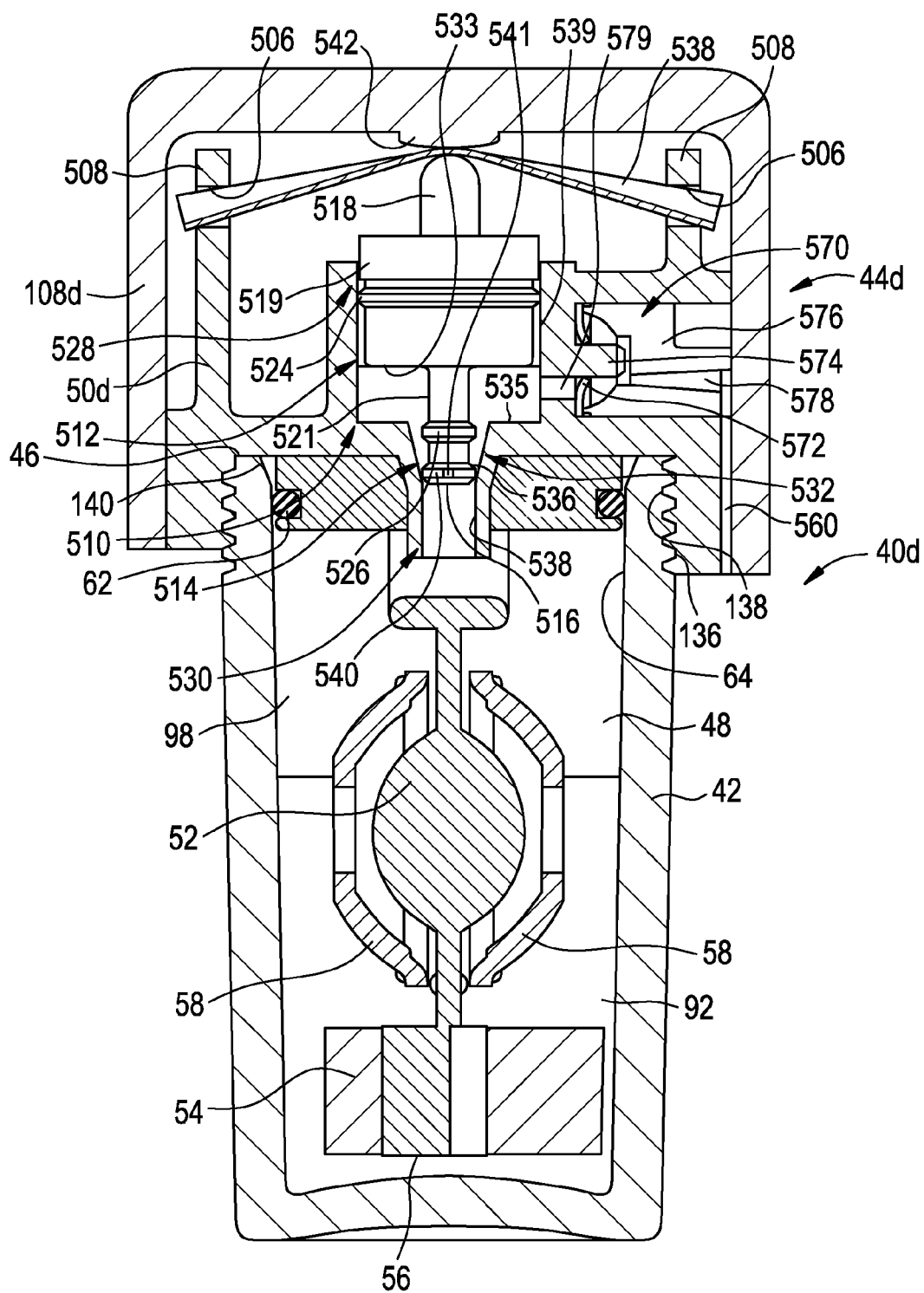

FIGS. 22 and 23 are cross-sectional views of a contact lens disinfecting system 40d which is in accordance with yet another embodiment of the present invention. The system 40d is also configured to create the desirable elevated pressure, oxygen saturation and sustained peroxide concentration conditions within its contact lens holding and reaction chamber, in order to enhance disinfection by additive effect as disclosed hereinabove. In many respects, the structure and operation of the contact lens disinfection system 40d shown in FIGS. 22 and 23 is similar to the contact lens disinfecting systems 40, 40a, 40b, 40c previously described. As such, identical reference numerals are used to identify identical parts. For example, much like the contact lens disinfecting systems 40, 40a, 40b, 40c, the contact lens disinfection system 40d includes a cup 42 and a cap assembly 44d which is configured to threadably engage the top 46 of the cup 42, and the cup 42 is conventional in that it is generally cylindrical and provides a reaction chamber 48 therein for disinfecting contact lenses.

The cap assembly 44d comprises a cap 108d which is affixed to a valve body 50d. The valve body 50d is preferably a single piece, multi-walled structure and is configured to threadably engage the top 46 of the cup 42. A stem 52 is attached to and hermetically sealed to the valve body 50d. A catalyst 54 (conventional with regard to composition), sized to complete the reaction within an appropriate time, is affixed to the bottom 56 of the stem 52. Additionally, contact lens retaining baskets 58 are disposed on the stem 52. The retaining baskets 58 are configured to pivot open and closed, in order to receive contact lenses, and maintain the contact lenses in a space 60 which is provided between the stem 52 and the retaining baskets 58. A sealing member 62 is provided on the stem 52, for sealing against an internal wall 64 of the cup 42.

Apertures 506 are provided on the valve body 50d for retaining a control spring 538 proximate spring supports 508 (said control spring 538 preferably being identical in nature to the control spring 238 of the system 40a shown in FIGS. 10 and 11 and previously described). As will be described more fully later hereinbelow, a plunger 512 is configured to traverse up and down relative to the valve body 50d, and the control spring 538 works to limit and control upward movement of a plunger 512 relative to the valve body 50d.

The valve body 50d includes a plunger receptacle 510, and the plunger 512 is disposed in the plunger receptacle 510. The plunger 512 preferably includes a domed-shaped top surface 518 which extends upward from a generally cylindrical portion 519, and a stem portion 521 extends downward from the generally cylindrical portion 519. The plunger 512 can take many forms, but one preferred structure of the plunger 512 provides that the plunger 512 consists of a plastic body having a piston 514, formed of an elastomeric material, molded onto the plastic body to provide a plunger seal 524 and a piston seal 526. While the plunger seal 524 is provided on the generally cylindrical portion 519 of the plunger 512, the piston seal 526 is provided on the stem portion 521 which extends downward. While the piston seal 526 operates within and seals against an internal wall 538 in a piston cylinder area 530 of the valve body 50d, the plunger seal 524 operates within and seals against an internal wall 539 in a plunger cylinder area 528 of the valve body 50d. A transition area 532 is provided between the plunger cylinder area 528 and the piston cylinder area 530.

As discussed above, the plunger 512 is configured to traverse up and down within the receptacle 510 of the valve body 50d, and the control spring 538 works to limit and control upward movement of the plunger 512 relative to the valve body 50d. With regard to downward movement of the plunger 512, a bottom surface 533 of the generally cylindrical portion 519 of the plunger 512 is configured to limit downward movement of the plunger 512 in the receptacle 510, via contact with the internal wall 535 of the valve body 50b as shown in FIG. 22.

At the end 516 of the plunger 512 is a plunger guide 536, and the plunger guide 536 is configured to contact the internal wall 538 of the valve body 50d, in the piston cylinder area 530, and align the piston 514. Preferably, one or more flats 540, and/or a vent notch 541 and/or other structure, are provided on the plunger guide 536, to allow for the flow of pressurized oxygen from headspace 98 to enter plunger cylinder area 528 through the transition area 532, and bear next upon the larger diameter plunger seal 524 to provide additional force against control spring 538, thereby forcing it against a stop boss 542 (see FIG. 23) which is provided on the underside of the cap 108d.

The contact lens disinfecting system 40d includes a pressure control valve 570 which is comprised of a flapper valve 572, a post 574, and a plug 576 mounted to the valve body 50d. As the piston seal 526 rises in response to the gas pressure it is receiving, it slides out of sealing engagement with internal wall 538 of the piston cylinder area 530, and enters transition area 532, thereby allowing gas in the headspace 98 to vent through the pressure control valve 570, and out a port 578 which is provided in the plug 576. Specifically, the venting gas travels through an opening 579 in the valve body 50d, along port 578, and out a space 560 which is provided between the cap 108d and the valve body 50d. Vent valves similar to the pressure control valve 570 have been previously employed to facilitate venting of contact lens cases (see U.S. Pat. No. 4,956,156).

From a downward starting position as shown in FIG. 22, upward longitudinal movement of plunger 512 traversing within valve body 50d is limited by the control spring 538, which is configured to detain the plunger's movement until internal pressure reaches a certain point. Once a high enough internal pressure (i.e., in headspace 98) is reached, the plunger 512 moves upward, resulting in the gas flowing past the plunger guide 536 (i.e., by means of the flats 540, vent notch 541, and/or other structure), and bearing upon the generally cylindrical portion 519 of the piston 514. The plunger 512, in turn, transfers the load to the control spring 538 by means of the top surface 518 of the plunger 512 bearing against the control spring 538. Just like the control spring 238, the control spring 538 is "U"-shaped in cross-section and acts as a beam to transfer the pressure-induced load from abutting top surface 518 to control spring supports 508, thereby resisting upward movement of plunger 512.

As pressure within headspace 98 against piston 512 (from the ongoing disproportionation of the solution 92) rises to the desirable 180 p.s.i. to 366 p.s.i. high pressure condition previously described, the plunger 512 (with top surface 518) gains sufficient force to overcome control spring 538. In response, the "U"-shape of the control spring 538 begins to deform in a manner in which the cross-sectional height of the "U"-form becomes smaller, causing the beam strength of the control spring 538 to decline. When the force delivered by the plunger 512 to the control spring 538 reaches the maximum beam strength of control spring 538, the spring 538 flattens and buckles as its cross-section diminishes, thereby allowing plunger 512 (with piston 514 and top surface 518) to move upward until the spring 538 abuts the stop 542 on the cap 108d, as shown in FIG. 23. In this deformed condition, the control spring 538 offers plunger 514 significantly lower resistance. A typical shape transition in response to bending loads by a spring such as control spring 538 can be more clearly understood by comparing the shape of control spring 538 in FIG. 22 with its shape shown in FIG. 23, and the spring's resistance forces during such a transition in shape can more clearly be understood by viewing FIG. 13. As shown in FIG. 13, a spring such as the control spring 538 shown in FIGS. 22 and 23 demonstrates its maximum beam strength of 2.69 units when the plunger 512 bearing upon it reaches 0.090 inch of travel and its minimum beam strength of 0.64 units, or less than 25% of the maximum, at 0.105 inch of plunger travel just 0.025 of an inch later.

Decompression initiates as deformation of the control spring 538 allows the piston 514 to begin to exit the piston cylinder area 530 and enter the transition area 532, thereby allowing pressurized oxygen bearing on the piston 514 to enter the transition area 532. The plunger guide 536, having one or more vent flats 540, and/or vent notches 541 and/or other structure to allow gas flow to bypass, remains engaged with the internal wall 538 in the piston cylinder area 530 to stabilize the plunger 512 as it traverses upwards against the control spring 538. Oxygen gas under pressure flowing past piston 512 travels through the transition area 532, enters the plunger cylinder area 528, and bears next upon the generally cylindrical portion 519 of the plunger 512 and its plunger seal 524, providing additional force against the control spring 538, pressing it against the stop 542 on the cap 108d. If, for example, the piston 514 were 0.125 inches in diameter, the force delivered by the plunger 512 to the control spring 538 in response to a headspace pressure of 220 p.s.i. would be 2.7 lbs. If, by further example, the plunger cylinder area 528 were 0.357 inches in diameter and gas at the same pressure of 220 p.s.i. entered below the plunger seal 524, the potential immediate force against the control spring 538 could increase to 22 pounds. This increased force would only be momentary, however, due to provision of the one way, low pressure, pressure-sensitive, pressure control valve 570.

Gas entering the plunger cylinder area 528, and contained by the plunger seal 524, can only escape to the ambiance by means of pressure control valve 570. The flapper valve 572, retained on the post 574 by plug 576, communicates with the plunger cylinder area 528 through the opening 579 which is provided in the valve body 50d. Decompression of the headspace 98 is precipitated as oxygen gas under pressure against flapper valve 572 is allowed to vent at the annular junction between the flapper 572 and the post 574, and exit to the ambiance through port 578 and out space 560, once a threshold pressure of 20 p.s.i. to 32 p.s.i., for example, has been reached. Such venting ceases as the flapper 572 reseals against the post 574, after pressure against it has decreased to a level below that of the original threshold pressure, which for this example would be approximately 3 p.s.i. to 8 p.s.i. lower than the threshold pressure. In the immediate example, a resealing pressure of 12 p.s.i. bearing against plunger 512 would exert 1.2 pounds of force against the control spring 538. This force would be adequate to hold control spring 538 solidly against spring stop 542, as can be seen in FIG. 23, wherein control spring 538 requires only 0.66 pounds of force to maintain its deflection of 0.11 inches and 0.81 pounds of force to maintain its deflection of 0.15 inches. Pressure within headspace 98 after initial venting fluctuates between the pressure control valve's vent pressure and its resealing pressure, but will not normally drop below its resealing pressure as decomposition of hydrogen peroxide 92 continues to completion. Assuming the control spring 538 performs as shown in FIG. 13, if resealing pressure of the control valve 570 ever dropped below 6.6 p.s.i., or in the event that flapper 572 failed to reseal to the post 574, control spring 538 would push the plunger 512 downward, and the piston 514 would re-engage with the internal wall 538 of the piston cylinder area 530, thereby sealing headspace 98 and the solution 92 from communication with the ambiance to prevent any risk of entry by foreign matter or organisms. In normal use, barring any failure of control valve 570, oxygen gas pressure within the headspace 98 would remain at a level between the pressure control valve's vent pressure and its resealing pressure, keeping plunger 512 upward and control spring 538 deflected until cap 44 is unscrewed sufficiently to allow gas to pass between sealing member 62 and chamfer 140 to relieve the pressure.

Much like as with the contact lens disinfecting systems 40, 40a, 40b, 40c, the contact lens disinfection system 40d shown in FIGS. 22 and 23 provides that in use, approximately 10 milliliters of hydrogen peroxide solution 92 is poured into the cup 42, the retaining baskets 58 on the stem 52 are pivoted open, contact lenses are placed onto the stem 52, and then the retaining baskets 58 are pivoted closed in order to retain the contact lenses in space 60. Finally, the stem 52 is inserted into the cup 42, and the cap assembly 44d is threaded onto the top 46 of the cup 42. Preferably, the cup 42 is sized such that when the cap assembly 44d is threaded onto the top 46 of the cup 42, with 10 milliliters of hydrogen peroxide 92 being contained in the cup 42, there remains 4 cc's of headspace 98 above the hydrogen peroxide 92, for containment of oxygen gas which evolves during the disinfection process. While providing 4 cc's of headspace is one possibility, the volume of the headspace 98 can be varied as can the surface area of the catalyst 54, in order to achieve a desired internal pressure to control the reaction as previously discussed.

Once the catalyst 54 has been introduced to the hydrogen peroxide solution 92, and the contact lens disinfecting system 40d is sealed by threading the cap assembly 44d onto the top 46 of the cup 42, the system 40d appears as shown in FIG. 22, and pressure in the reaction chamber 48 starts to increase. From the starting position shown in FIG. 22, longitudinal movement of the plunger 512 traversing within the valve body 50d is limited by the control spring 538, which is configured to detain the plunger's movement until pressure within headspace 98 enters the piston cylinder area 530 and bears upon the piston 514 with sufficient force to exceed the beam strength of control spring 538 and thereby initiate its flattening and buckling. As this deformation of the control spring 538 occurs, piston 514 exits piston cylinder area 530 and traverses into the transition area 532. The plunger guide 536 remains engaged with the internal wall 538 of the valve body 50d in the piston cylinder area 530 in order to stabilize the plunger 512.

Much like contact lens disinfecting systems 40, 40a, 40b, 40c, the contact lens disinfecting system 40d shown in FIGS. 21 and 22 preferably provides that sufficient threads 136, 138 are provided on the cup 42 and the cap assembly 44d, respectively, to allow the sealing member 62 on the stem 52 to pass a chamfer 140 which is provided at the top 46 of the cup 42, in order to relieve any residual pressure that may be present prior to final unscrewing of the cap assembly 44d from the cup 42. Conversely, during installation of the cap assembly 44d, sufficient thread engagement is provided before the sealing member 62 on the stem 52 passes below the chamfer 140, in order to assure that adequate structure is engaged for containment of pressure generated during disinfection.

Figure 24:
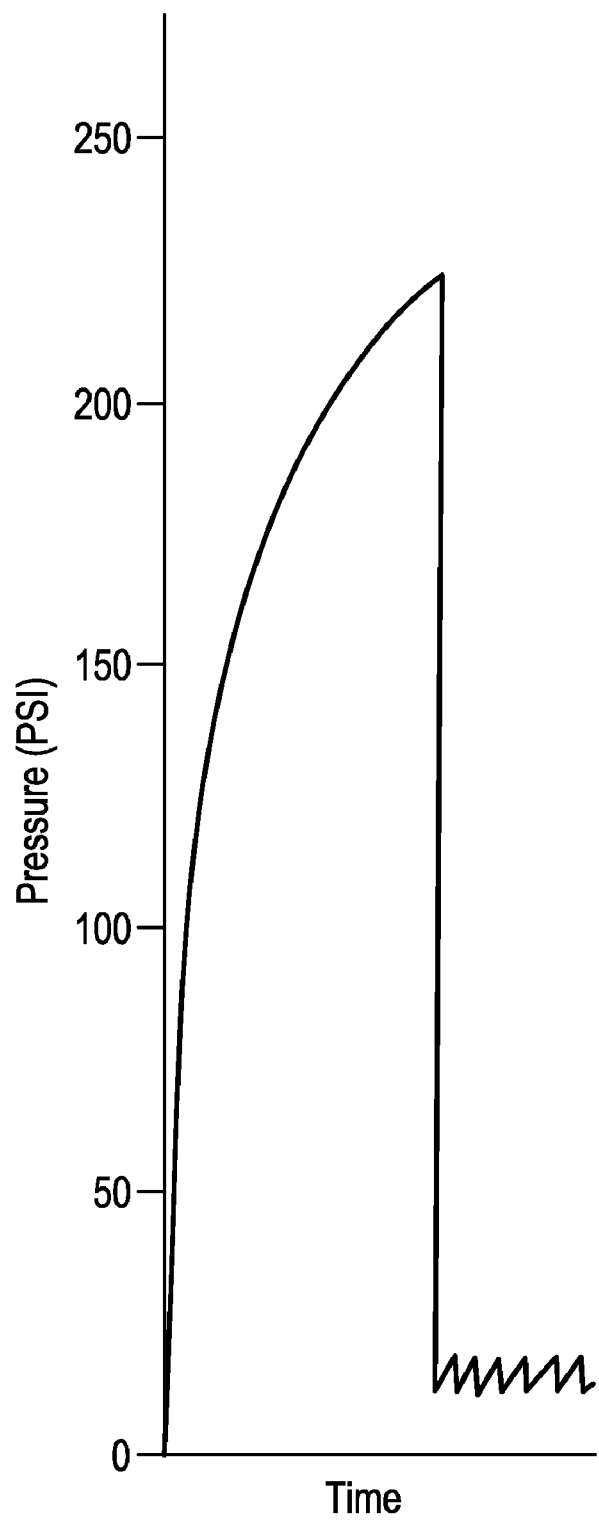
FIG. 24 is a graph which shows the change in pressure over time during the disinfection process, when the contact lens disinfecting system shown in FIGS. 22 and 23 is used.

Decompression provides a further additive effect to the disinfection process when oxygen occupying the headspace 98 is allowed to escape by movement of the piston 514 and saturated oxygen within the hydrogen peroxide disinfection solution boils off, thereby allowing pressure in the headspace 98 to drop to a point slightly above the atmospheric ambient much more quickly than a pathogenic organism could adjust to maintain dynamic equilibrium. During the pressurization and decompression phases of the process, including venting to atmosphere, pressure within the headspace 98 initially rises to the high pressure level established by the control spring 538, and then precipitously drops during venting after which it rises and falls slightly, as shown in FIG. 24, as it responds to low pressure control provided by the reaction of the plunger 512 in response to the pressure control valve's venting and resealing pressures. Concurrent with initial high pressure relief, the rate of catalytically-inspired disproportionation of the hydrogen peroxide solution 92 increases beyond that just prior to pressure relief as the activation energy level is lowered. Mixing currents are also generated as oxygen boils from the solution 92, and these resulting currents initially speed the catalytic decomposition by disturbing stratification to bring more peroxide molecules into contact with the catalyst 54. Oxygen continues to be evolved into headspace 98 and be controlled by the cyclic venting of the control valve 570 as final decomposition of the solution 92 lowers peroxide concentration toward an ocularly safe level for use of the lenses disinfected within.

Figure 25:
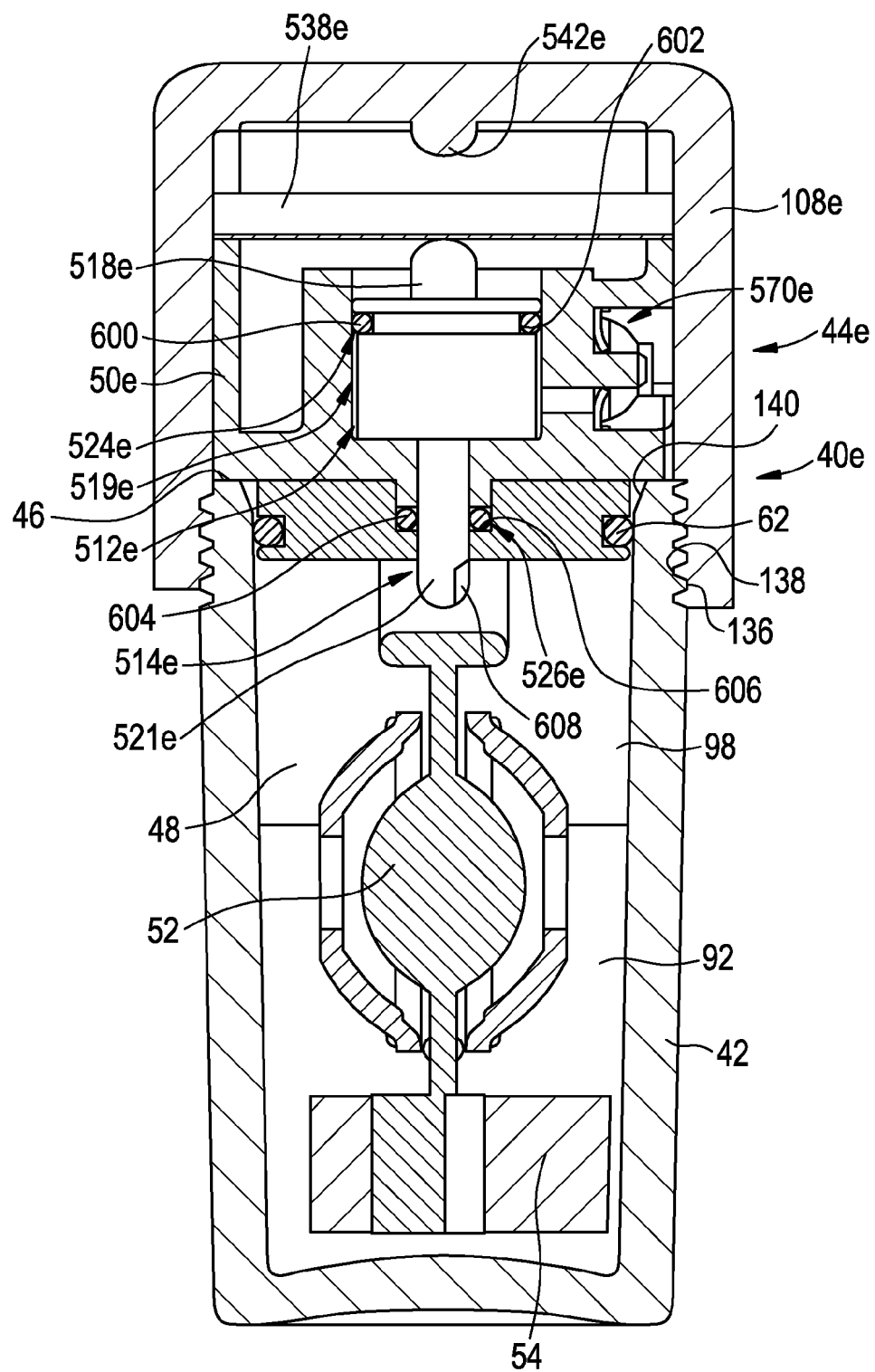
FIGS. 25 and 26 are cross-sectional views of a contact lens disinfecting system which is in accordance with another embodiment of the present invention.
Figure 26:
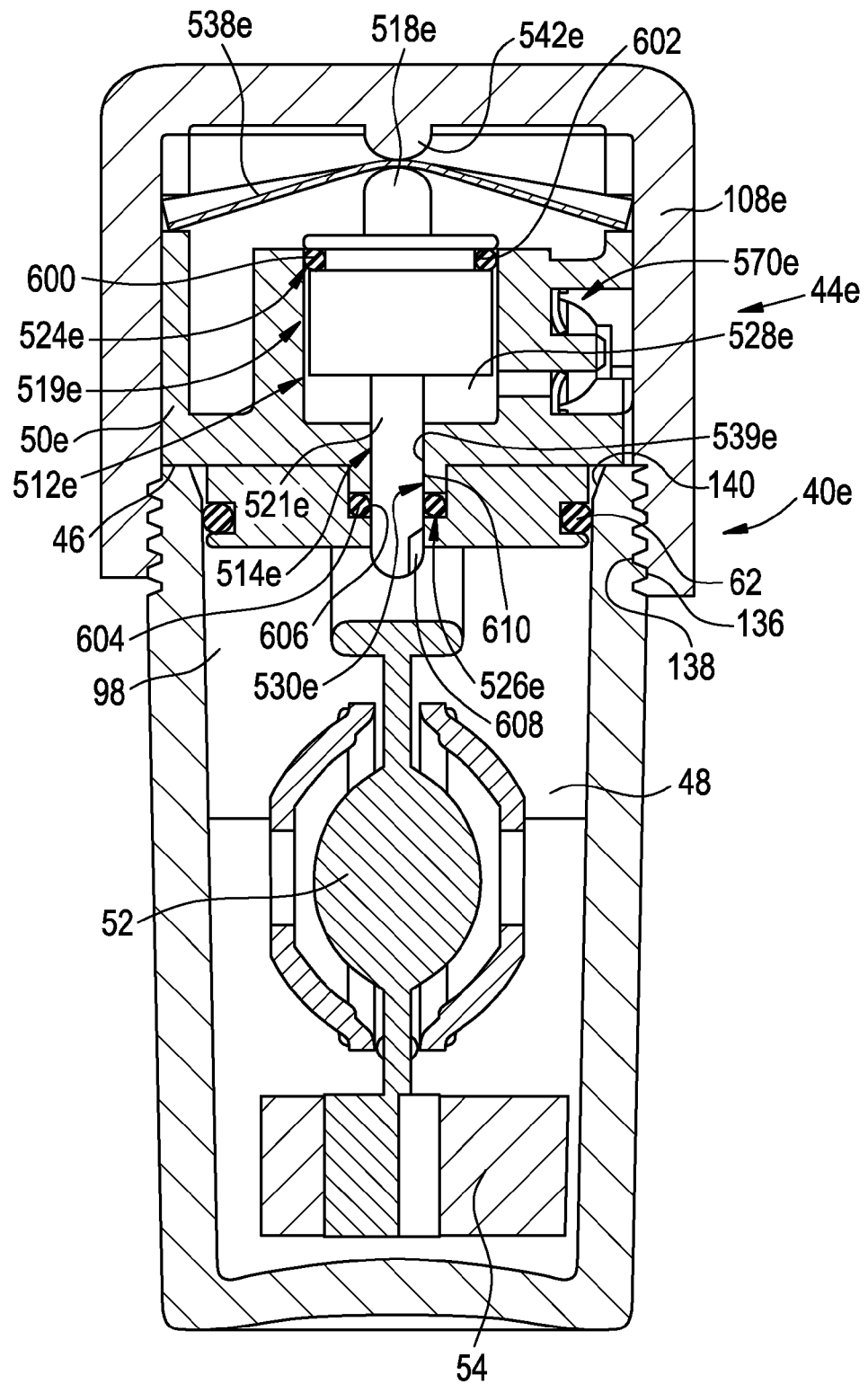

FIGS. 25 and 26 are cross-sectional views of a contact lens disinfecting system 40e which is in accordance with yet another embodiment of the present invention. The system 40e is very much like the system 40d shown in FIGS. 22 and 23, and includes a cap assembly 44e that includes a cap 108e which is affixed to a valve body 50e, and there is a control valve 570e on the valve body 50e. The system 40e includes a plunger 512e and a piston 514e is provided at the lower end of the plunger 512e in the form of a downwardly-extending portion 521e. However, unlike the system 40d shown in FIGS. 22 and 23, the plunger seal 524e of the system 40e is provided in the form of a sealing member 600 which is retained in a groove 602 on the generally cylindrical portion 519e of the plunger 512e, and the piston seal 526e is provided in the form of a sealing member 604 which is retained in a receiving groove 606 which provided between the valve body 50e and the stem 52. Both sealing members 600, 604 are preferably formed of a suitable elastomeric material. A longitudinal slot 608, flat, reduced diameter section, and/or other structure is provided on the downwardly-extending portion 521e of the plunger 512e for allowing the passage of gas from the headspace 98, as will be described more later hereinbelow.

Just like the system 40d shown in FIGS. 22 and 23, the plunger 512e of the system 40e shown in FIGS. 25 and 26 can traverse up and down relative to the valve body 50e, and a U-shaped (in cross-section) control spring 538e controls upward longitudinal movement of the plunger 512e. The control spring 538e of the system 40e shown in FIGS. 25 and 26 is structured and acts much the same way as the other "U"-shaped control springs previously described. As such, FIG. 13 and the descriptions hereinabove relating to such a spring are applicable.

In operation, once the catalyst 54 has been introduced to the hydrogen peroxide solution 92, and the contact lens disinfecting system 40e is sealed by threading the cap assembly 44e onto the top 46 of the cup 42, the system 40e appears as shown in FIG. 25, and pressure in the reaction chamber 48 starts to increase. From the starting position shown in FIG. 25, longitudinal movement of the plunger 512e traversing within the valve body 50e is limited by the control spring 538e, which is configured to detain the plunger's movement until pressure within headspace 98 is sufficient to push up on the plunger 512e such that the plunger 512e moves upward (against the spring 538e up to the stop 542e on the cap 108e) and the slot 608, flat, reduced diameter section, and/or other structure slides up past the piston seal 526e, as shown in FIG. 26. The gas in the headspace 98 then travels along the space 610 which is provided between the piston 514e and the internal wall 539e of the piston cylinder area 530e, enters the plunger cylinder area 528e, and is stopped by the plunger seal 524e where the additional surface area of the plunger 512e works to effectively increases the force that the top surface 518e applies against the control spring 538e.

Much like with the system 40d, the system 40e shown in FIGS. 25 and 26 provides that if, for example, the piston 514e were 0.125 inches in diameter, the top surface 518e of the plunger 512e would exert a bending force against the control spring 538e of 2.7 lbs once 220 p.s.i. of pressure is reached within headspace 98. By comparison, the plunger 512e at 0.357 inches in diameter would have the potential to exert 22 lbs of force against the control spring 538e when exposed to 220 p.s.i. of pressure. This increased force would only be momentary, however, due to provision of the one way, low pressure, pressure-sensitive, pressure control valve 570e.

Gas entering the plunger cylinder area 528e, and contained by the plunger seal 524e, can only escape to the ambiance by means of pressure control valve 570e, as described above in connection with the system 40d shown in FIGS. 22 and 23. At 12 p.s.i., the force exerted by the plunger 512e would be sufficient to keep the spring 538e deflected and maintain communication between the headspace 98 and the control valve 570e.

As disclosed above with regard to the system 40d, the system 40e shown in FIGS. 25 and 26 provides that pressure initially rises to the high pressure established by the control spring 538e, and then drops precipitously during venting after which the pressure rises and falls slightly, as shown in FIG. 24, as it responds to low pressure control provided by the control valve 570e. After initial venting, pressure within the headspace 98 fluctuates between the pressure control valve's vent pressure and its resealing pressure, but does not normally drop below its resealing pressure. This low level rising and falling pressure pattern continues for several hours after decompression as decomposition of the hydrogen peroxide 92 continues to a lower concentration level, down to an ocularly safe level.

Assuming the control spring 538e performs as shown in FIG. 13, if resealing pressure of the control valve 570e ever dropped below 6.4 p.s.i., or in the event that the control valve 570e failed to reseal, control spring 538e would push the plunger 512e downward, causing the longitudinal slot 608, flat, reduced diameter section, and/or other structure on the plunger 512e to drop below the piston seal 526e, as shown in FIG. 25, thereby effectively sealing the headspace 98 and solution 92 from communication with the ambience and preventing any risk of entry by foreign matter or organisms.

As with the other systems 40, 40a, 40b, 40c, 40d, the system 40e shown in FIGS. 25 and 26 provides that sufficient threads 136, 138 are on the cup 42 and the cap assembly 44e, respectively, to allow the sealing member 62 on the stem 52 to pass a chamfer 140 which is provided at the top 46 of the cup 42, in order to relieve any residual pressure that may be present prior to final unscrewing of the cap assembly 44e from the cup 42. Conversely, during installation of the cap assembly 44e, sufficient thread engagement is provided before the sealing member 62 on the stem 52 passes below the chamfer 140, in order to assure that adequate structure is engaged for containment of pressure generated during disinfection.

As with the other systems 40, 40a, 40b, 40c, 40d, the system 40e shown in FIGS. 25 and 26 provides that decompression resulting from the release of high pressure within the system 40e provides a further additive effect to the disinfection process by creating additional stress against the cell membranes of pathogenic organisms undergoing denaturation previously discussed hereinabove.

Each of the systems 40, 40a, 40b, 40c, 40d, 40e described hereinabove provides that decompression resulting from release of high pressure within the system provides a further additive effect to the disinfection process when oxygen occupying headspace 98 is allowed to escape in a controlled manner and saturated oxygen within the hydrogen peroxide disinfection solution boils off thereby allowing pressure in headspace 98 to drop to the controlled low pressure level much more quickly than a pathogenic organism could adjust in order to maintain dynamic equilibrium.

Figure 27:
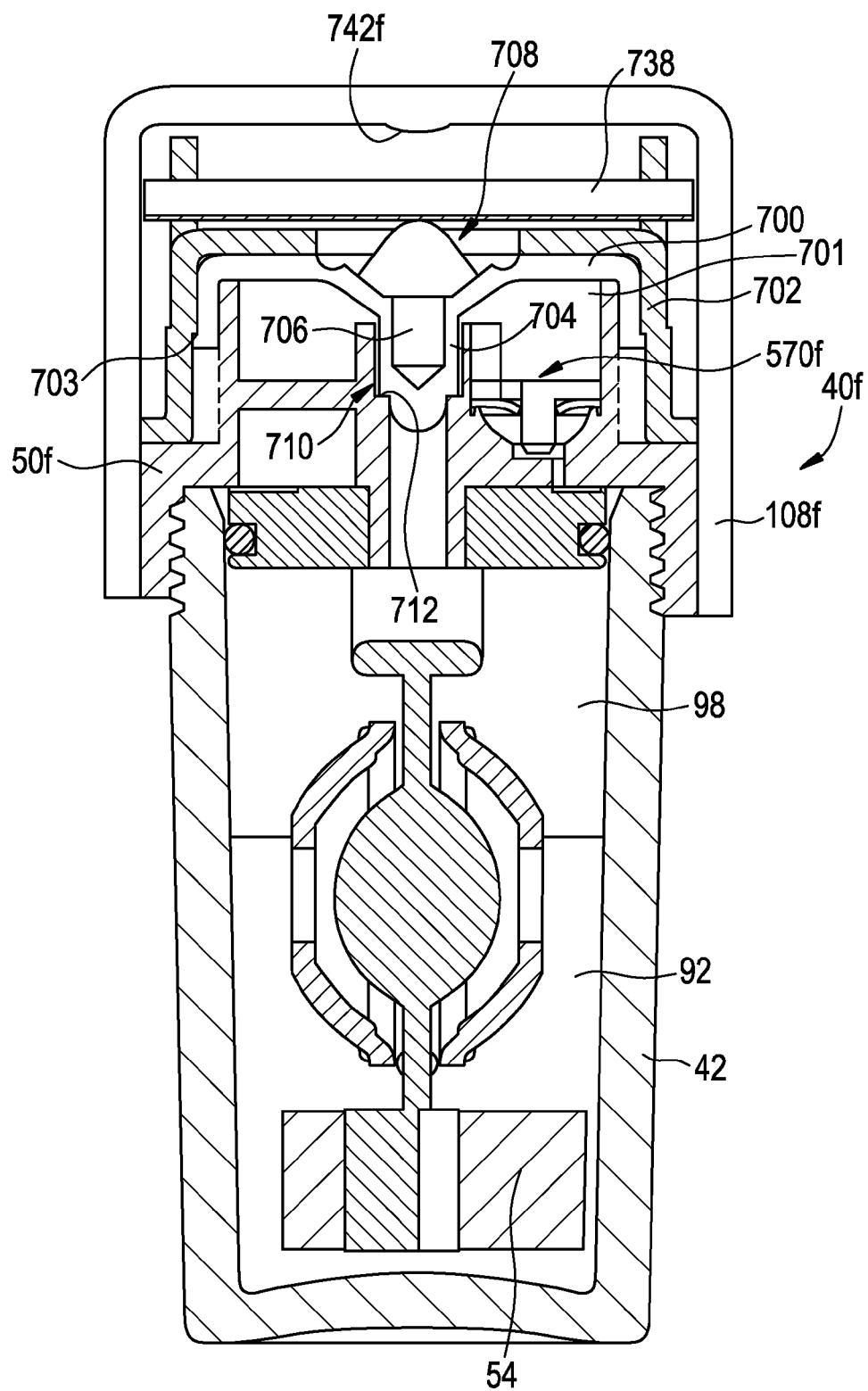
FIGS. 27 and 28 are cross-sectional views of a contact lens disinfecting system which is in accordance with still yet another embodiment of the present invention.
Figure 28:
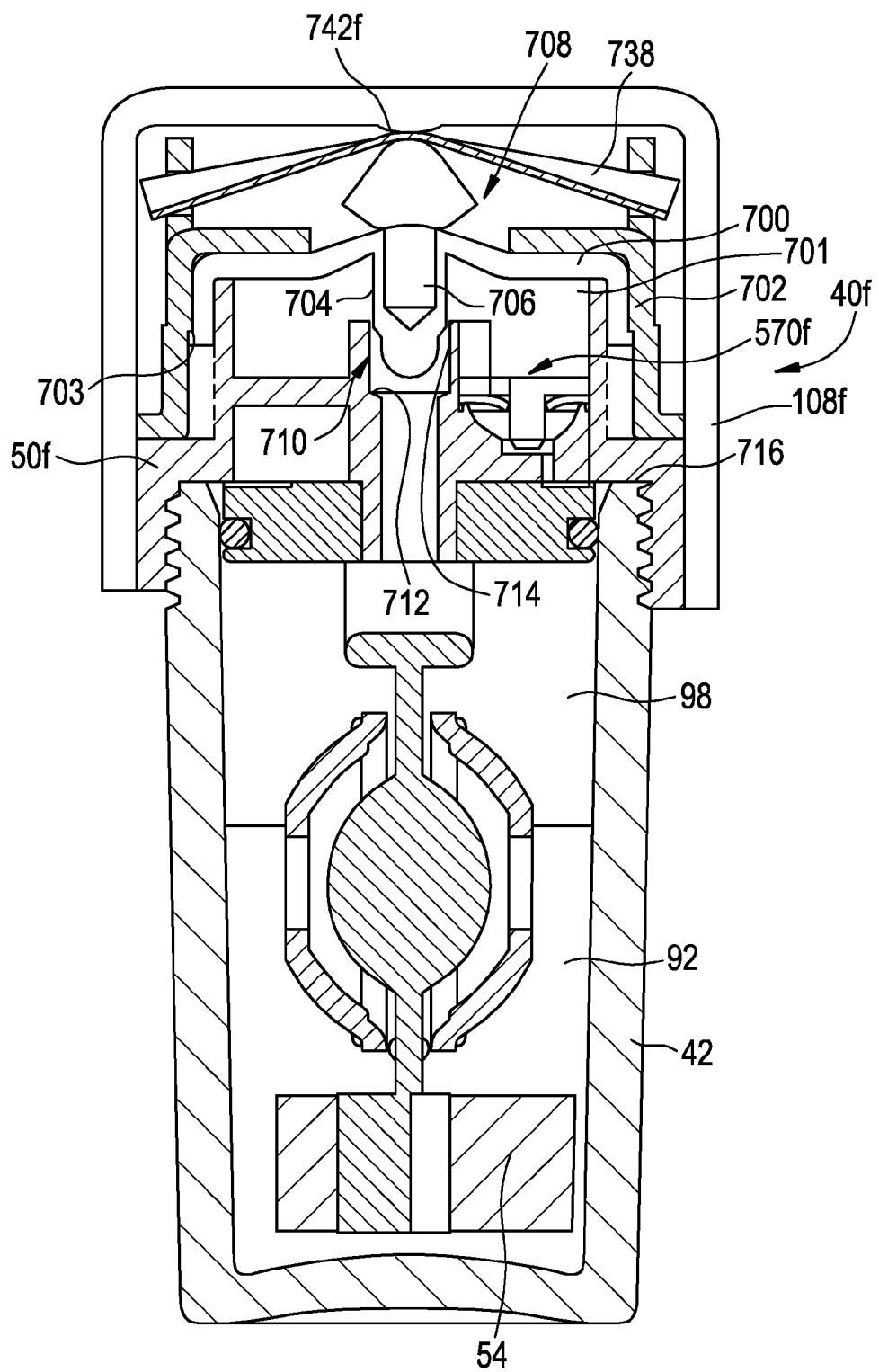

It should be pointed out that any of the systems 40, 40a, 40b, 40c, 40d, 40e described hereinabove can be redesigned to include a diaphragm. FIGS. 27 and 28 illustrate an example wherein the systems 40d, 40e shown in FIGS. 22, 23, 25 and 26 have been redesigned in this fashion. As shown in FIGS. 27 and 28, the system 40f includes a diaphragm 700 located in a diaphragm chamber 701, in the form of an elastomeric member which is held in place between a valve body 50f and a spring-retaining member 702. As shown, preferably the spring-retaining member 702 includes a shoulder 703 which tends to keep the diaphragm 700 retained. A portion 704 of the diaphragm 700 is engaged with an extending portion 706 of a plunger 708. The plunger 708 is moveable up and down, generally into and out of, a plunger-receiving receptacle 710 of the valve body 50f. When the plunger 708 is in a first position, as shown in FIG. 27, wherein the extending portion 706 of the plunger 708 is seated in the plunger-receiving receptacle 710, there is no venting of the system 40f through the pressure control valve 570f. In this position, the diaphragm 700 seals with an internal shoulder 712 on the valve body 50f, and the pressure within the headspace 98 is allowed to increase while the solution 92 reacts to the catalyst 54. However, once pressure in the system 40f increases to a sufficiently high enough pressure, the pressure in the headspace 98 pushes the plunger 708 up into the position shown in FIG. 28. In this position, the diaphragm chamber 701 is no longer sealed from headspace 98 with the internal shoulder 712 on the valve body 50f, and the system 40f is allowed to vent along a space 714 provided between the diaphragm 700 and the valve body 50f, into diaphragm chamber 701, and out the pressure control valve 570f along interface 716 between the valve body 50f and the top of the cup 42. Other the difference of using a diaphragm to effectively take the place of the plunger having an over-molded surface, the system 40f is structured and operates similar to both systems 40d and 40e. As such, the system 40f includes, for example, a cap 108f having a stop 742f as well as includes a U-Shaped control spring 738 which is identical to the control spring 238 shown on FIG. 12 and described at length above in connection with other embodiments.

While specific embodiments of the present invention are shown and described, it is envisioned that those skilled in the art may devise various modifications of the present invention without departing from the spirit and scope of the present invention.

What is claimed is:

1. A disinfecting system for using solution and a catalyst to disinfect an object, said disinfecting system comprising: a cup configured to retain the solution therein; and a cap assembly engageable with the cup and configured to retain the object as well as the catalyst, said cap assembly comprising a shiftable member, said shiftable member comprising a plunger, a plunger cap on the plunger, and a biasing member between the plunger and the plunger cap, wherein the plunger is shiftable between a first position for sealing the disinfecting system and a second position for venting the disinfecting system, and a control spring in contact with the plunger cap when the plunger is in the second position and configured to bias the plunger from the second position to the first position, said plunger cap being between the plunger and the control spring, wherein the biasing member is configured to bias the plunger away from the plunger cap, wherein the disinfecting system is configured such that pressure within the disinfecting system increases as a result of the solution reacting to the catalyst, during which time additive effect enhances disinfection of the object, and during which time the plunger is in said first position, wherein the disinfecting system is configured such that pressure within the disinfecting system further increases, thereby causing the plunger to shift from the first position to the second position, thereby causing venting of the disinfecting system, and wherein the disinfecting system is configured such that pressure within the disinfecting system decreases during venting, thereby causing the biasing member to push the plunger away from the plunger cap, causing the plunger to shift from the second position to the first position, thereby causing resealing of the disinfecting system, wherein the disinfecting system is configured such that pressure within the disinfecting system increases again, thereby causing the plunger to shift from the first position to the second position, thereby causing venting of the disinfecting system, wherein the disinfecting system is configured such that pressure within the disinfecting system decreases again during venting, thereby causing the control spring to push and move the shiftable member, thereby causing resealing of the disinfecting system.

2. A disinfecting system as recited in claim 1, wherein the control spring has a U-shaped cross section.

3. A disinfecting system as recited in claim 1, wherein the cap assembly further comprises a valve body which is configured to engage a top of the cup.

4. A disinfecting system as recited in claim 3, wherein the cap assembly further comprises a spring-retaining member which retains said control spring and is affixed to said valve body.

5. A disinfecting system as recited in claim 4, wherein said valve body is configured to contact and restrict further movement of the plunger in the first position, and wherein the valve body comprises latching members through which the plunger cap is moveable, wherein the latching members are configured to prevent the plunger cap from moving therepast unless sufficient pressure is reached in the system.

6. A disinfecting system as recited in claim 5, wherein said system is configured such that the plunger cap becomes trapped above the latching members.

7. A disinfecting system as recited in claim 4, wherein the spring-retaining member comprises m least one stop which is configured to contact and arrest further movement of the plunger during venting of the system.

8. A disinfecting system as recited in claim 3, wherein said valve body is configured to contact and restrict further movement of the plunger in the first position.

9. A disinfecting system as recited in claim 1, wherein the plunger includes a venting feature.

10. A disinfecting system as recited in claim 9, wherein said venting feature comprises a longitudinal slot.

11. A disinfecting system as recited in claim 1, wherein the cap assembly further comprises a valve body which is configured to engage a top of the cup and a stem which is engaged with the valve body, wherein a sealing member is disposed between the stem and the valve body, wherein the plunger includes a venting feature, and wherein the venting feature passes said sealing member as said plunger shifts from the first position to the second position, thereby allowing venting of the system.

12. A disinfecting system as recited in claim 11, wherein the valve body provides a vent passage, wherein the venting feature on the plunger passes said sealing member as said plunger shifts from said first position to said second position, thereby allowing venting of the system along said vent passage.

13. A disinfecting system as recited in claim 1, wherein the cap assembly further comprises a valve body which is configured to engage a top of the cup and a stem which is engaged with the valve body, wherein a first sealing member is disposed between the stem and the valve body, wherein the plunger includes a venting feature, wherein the venting feature on the plunger passes said first sealing member as said plunger shifts between said first and second positions, wherein a second sealing member is disposed on the plunger and seals against the valve body.

14. A disinfecting system as recited in claim 11, wherein said valve body provides a vent passage, wherein the venting feature passes said first sealing member as said plunger shifts from the first position to the second position, thereby allowing venting of the system along said vent passage.

15. A disinfecting system as recited in claim 1, further comprising a first sealing member disposed between a valve body and a stem, and a second sealing member on the plunger.

16. A disinfecting system as recited in claim 15, wherein a vent passage is provided on the valve body, disposed between the first and second sealing members.

17. A disinfecting system as recited in claim 1, wherein the cap assembly comprises a cap and a valve body, wherein the cap comprises a lip which is configured to retain the cap on the valve body.

18. A disinfecting system as recited in claim 1, wherein the cap assembly comprises a cap and a valve body, wherein a castellated structure is on the valve body and castellated structure is on an inside surface of the cap, wherein the cap is spring-biased away from the valve body, but is pushable toward the valve body, thereby causing the castellated structure on the valve body to engage the castellated structure on the inside surface of the cap, such that subsequent turning of the cap causes the cap assembly to disengage the cup.

19. A disinfecting system as recited in claim 18, wherein the cap is configured to contact and move the shiftable member upon the cap being pushed down.

20. A disinfecting system as recited in claim 18, wherein the cap comprises a post which is configured to push the shiftable member down when the cap is pushed down.

* * * * *